US009206427B2

(12) United States Patent
Shipp et al.

(10) Patent No.: US 9,206,427 B2
(45) Date of Patent: Dec. 8, 2015

(54) COMPOSITIONS, KITS, AND METHODS FOR THE MODULATION OF IMMUNE RESPONSES USING GALECTIN-1

(75) Inventors: Margaret A. Shipp, Wellesley, MA (US); Przemyslaw Juszczynski, Jamaica Plain, MA (US); Jing Ouyang, Chestnut Hill, MA (US); Jeffery Kutok, Natick, MA (US); Scott Rodig, Westwood, MA (US); Gabriel Rabinovich, Ciudad de Buenos Aires (AR)

(73) Assignees: Dana-Farber Cancer Institute, Inc., Boston, MA (US); CONICET, Buenos Aires (AR); Fundacion Sales, Buenos Aires (AR)

( * ) Notice: Subject to any disclaimer, the term of this patent is extended or adjusted under 35 U.S.C. 154(b) by 149 days.

(21) Appl. No.: 12/175,227

(22) Filed: Jul. 17, 2008

(65) Prior Publication Data

US 2009/0191182 A1 Jul. 30, 2009

Related U.S. Application Data

(60) Provisional application No. 60/959,830, filed on Jul. 17, 2007.

(51) Int. Cl.
| | | |
|---|---|---|
| *A61K 39/395* | (2006.01) | |
| *C12N 15/113* | (2010.01) | |
| *G01N 33/50* | (2006.01) | |
| *G01N 33/574* | (2006.01) | |
| *A61K 39/00* | (2006.01) | |

(52) U.S. Cl.
CPC .......... *C12N 15/1138* (2013.01); *A61K 39/395* (2013.01); *A61K 39/39533* (2013.01); *G01N 33/5011* (2013.01); *G01N 33/57407* (2013.01); *A61K 2039/585* (2013.01); *C12N 2310/14* (2013.01); *G01N 2500/00* (2013.01)

(58) Field of Classification Search
CPC .................. A61K 2039/505; A61K 47/48569; A61K 38/1709; A61K 39/0011; A61K 39/39558; A61K 51/1045; C07K 2316/96; C07K 2317/76; C07K 14/47; C07K 16/28
See application file for complete search history.

(56) References Cited

U.S. PATENT DOCUMENTS

| | | | |
|---|---|---|---|
| 7,011,947 | B2 | 3/2006 | Golub et al. |
| 2002/0006404 | A1* | 1/2002 | Hanna et al. ............... 424/142.1 |
| 2003/0109464 | A1 | 6/2003 | Huflejt et al. |
| 2004/0023855 | A1* | 2/2004 | John et al. ............... 514/8 |
| 2007/0207161 | A1* | 9/2007 | Ralph .................. 424/184.1 |

FOREIGN PATENT DOCUMENTS

| | | |
|---|---|---|
| WO | WO-99/12041 | 3/1999 |
| WO | WO-2004/030615 | 4/2004 |
| WO | WO 2006/108474 | * 10/2006 |
| WO | WO-2006/108474 | 10/2006 |
| WO | WO-2007/013807 | 2/2007 |

OTHER PUBLICATIONS

Garin et al., Blood, Mar. 1, 2007, vol. 109(5):2058-2065.*
Rush et al., Med. Pathol., 2000, vol. 13(12):1285-1293.*
Elola et al., J. Biomed. Sci., 2005, vol. 12:13-29.*
Seth et al., Ther. Deliv., 2012, vol. 3(2):245-261 (Abstract).*
Pei et al., Nature Methods, 2006, vol. 3:670-676.*
Baum et al., "Human Thymic Epithelial Cells Express an Endogenous Lectin, Galectin-1, which Binds to Core 2 O-Glycans on Thymocytes and T Lymphoblastoid Cells," Journal of Experimental Medicine, 181(3):877-887 (1995).
Cornillot et al., "Production and characterization of a monoclonal antibody able to discriminate galectin-1 from galectin-2 and galectin-3," Glycobiology, 8(5):425-432 (1998).
D'Haene et al., "The Differential Expression of Galectin-1 and Galectin-3 in Normal Lymphoid Tissue and Non-Hodgkin's and Hodgkin's Lymphomas," International Journal of Immunopathology and Pharmacology, 18(3):431-443 (2005).
Gabius et al., "Association of Galectin-1- but not Galectin-3-dependent Parameters with Proliferation Activity in Human Neuroblastomas and Small Cell Lung Carcinomas," Anticancer Research, 22(1A):407-408 (2002).
Giguere et al., "Carbohydrate triazoles and isoxazoles as inhibitors of galectins-1 and -3," Chemical Communications, pp. 2379-2381 (2006).
Juszczunski et al., "The AP1-dependent secretion of galectin-1 by Reed-Sternberg cells fosters immune privilege in classical Hodgkin lymphoma," Proceedings of the National Academy of Sciences, USA, 104(32):13134-13139 (2007).
La et al., "A Novel Biological Activity for Galectin-1," American Journal of Pathology, 163(4):1505-1515 (2003).
van den Brule, "Galectin-1 Modulates Human Melanoma Cell Adhesion to Laminin," Biochemical and Biophysical Research Communications, 209(2):760-767 (1995).
International Search Report dated Jan. 16, 2009 from PCT/US2008/070324.
Fluck et al., "Low-dose cyclophosphamide modulates galectin-1 expression and function in an experimental rat lymphoma model," Cancer Immunology, 56(2):237-248 (2006).
Garin et al., "Galectin-1: a key effector of regulation mediated by CD4+CD25+ T cells," Blood, 109(5):2058-2065 (2007).
Rodig et al., "AP1-Dependent Galectin-1 Expression Delineates Classical Hodgkin and Anaplastic Large Cell Lymphomas from Other Lymphoid Malignancies with Shared Molecular Features," Clinical Cancer Research, 24(11):3338-3344 (2008).

(Continued)

*Primary Examiner* — Xiaozhen Xie
(74) *Attorney, Agent, or Firm* — Foley Hoag LLP

(57) ABSTRACT

The present invention is based, in part, on the discovery that galectin-1 (Gal1) plays a role in immune disorders, including Hodgkin lymphoma. Accordingly, the invention relates to compositions, kits, and methods for detecting, characterizing, modulating, preventing, and treating immune disorders, e.g., Hodgkin lymphoma.

6 Claims, 5 Drawing Sheets

(56) References Cited

OTHER PUBLICATIONS

Rubenstein et al., "Targeted inhibition of galectin-1 gene expression in tumor cells results in heightened T cell-mediated rejection: A potential mechanism of tumor-immune privilege," Cancer Cell, 5(3):241-251 (2004).
Salvatore et al., "Galectin-1 gene expression and methylation state in human T leukemia cell lines," International Journal of Oncology, 17(5):1015-1018 (2000).
Velders et al., "Prospects for immunotherapy of acute lymphoblastic leukemia," Leukemia, 15(5):701-706 (2001).
International Search Report dated Jan. 27, 2009 from PCT/US2008/070328.
Abramson et al., "Advances in the biology and therapy of diffuse large B-cell lymphoma: moving toward a molecularly targeted approach," Blood, 106(4):1154-1174 (2005).
Amano et al., "The ST6Gal I Sialyltransferase Selectively Modifies N-Glycans on CD45 to Negatively Regulate Galectin-1-induced CD45 Clustering, Phosphatase Modulation, and T Cell Death," Journal of Biological Chemistry, 278(9):7469-7475 (2003).
Armstrong et al., "MLL translocations specify a distinct gene expression profile that distinguishes a unique leukemia," Nat. Genet., 30(1):41-47 (2002).
Baum et al., "Amelioration of graft versus host disease by galectin-1," Clin. Immunol., 109(3):295-307 (2003).
Benjamini et al., "Controlling the false discovery rate in behavior genetics research," Behav. Brain Res., 125(1-2):279-284 (2001).
Camby et al., "Galectin-1 modulates human glioblastoma cell migration into the brain through modifications to the actin cytoskeleton and levels of expression of small GTPases," J. Neuropathol. Exp. Neurol., 61(7):585-596 (2002).
Camby et al., "Galectin-1: a small protein with major functions," Glycobiology, 16(11):137R-157R (2006).
Derijard et al., "JNK1: a protein kinase stimulated by UV light and Ha-Ras that binds and phosphorylates the c-Jun activation domain," Cell, 76(6):1025-1037 (1994).
Drakos et al., "c-Jun expression and activation are restricted to CD30+ lymphoproliferative disorders," Am. J. Surg. Pathol., 31(3):447-453 (2007).
Gabrilovich, D.I., "Molecular mechanisms and therapeutic reversal of immune suppression in cancer," Curr. Cancer Drug Targets, 7(1):1 (2007).
Gandhi et al., "Expression of LAG-3 by tumor-infiltrating lymphocytes is coincident with the suppression of latent membrane antigen-specific CD8+ T-cell function in Hodgkin lymphoma patients," Blood, 108(7):2280-2289 (2006).
Gandhi et al., "Galectin-1 mediated suppression of Epstein-Barr virus-specific T-cell immunity in classic Hodgkin lymphoma," Blood, 110(4):1326-1329 (2007).
He et al., "Presentation of Galectin-1 by Extracellular Matrix Triggers T Cell Death," Journal of Biological Chemistry, 279(6):4705-4712 (2004).
Ishida et al., "Specific Recruitment of CC Chemokine Receptor 4-Positive Regulatory T Cells in Hodgkin Lymphoma Fosters Immune Privilege," Cancer Research, 66(11):5716-5722 (2006).
Jenner et al., "Increased alpha2,6-siaylation of surface proteins on tolerogenic, immature dendritic cells and regulatory T cells," Exp. Hematol., 34(9):1212-1218 (2006).
Juszcynski et al., "BAL1 and BBAP Are Regulated by a Gamma Interferon-Responsive Bidirectional Promoter and Are Overexpressed in Diffuse Large B-Cell Lymphomas with a Prominent Inflammatory Infiltrate," Molecular and Cellular Biology, 26(14):5348-5359 (2006).
Juszczynski, P., "Hodgkin's Lymphoma Reed Sternberg Cells Over Express the T-cell Inhibitory Carbohydrate-binding Lectin, Galectin 1: Role of AP-1 and Likely Mechanism of Tumor Immune Escape," Abstract for Presentation at the 48th ASH Annual Meeting, Orlando, Florida, Dec. 9-12, 2006.
Kanzler et al., "Hodgkin and Reed-Sternberg Cells in Hodgkin's Disease Represent the Outgrowth of a Dominant Tumor Clone Derived from (Crippled) Germinal Center B Cells," J. Exp. Med., 184:1495-1505 (1996).

Kuppers et al., "Biology of Hodgkin's lymphoma," Ann. Oncol., 13 Suppl 1:11-18 (2002).
Le et al., "Galectin-1: a link between tumor hypoxia and tumor immune privilege,"J. Clin. Oncol., 23(35):8932-8941 (2005).
Liu et al., "Galectins as modulators of tumour progression," Nat. Rev. Cancer, 5(1):29-41 (2005).
Loots et al., "rVISTA 2.0: evolutionary analysis of transcription factor binding sites," Nucleic Acids Research, 32:W217-W221 (2004).
Ludes-Meyers et al., "AP-1 blockade inhibits the growth of normal and malignant breast cells," Oncogene, 20:2771-2780 (2001).
Marshall et al., "Immunosuppressive regulatory T cells are abundant in the reactive lymphocytes of Hodgkin lymphoma," Blood, 103(5):1755-1762 (2004).
Mathas et al., "Aberrantly expressed c-Jun and JunB are a hallmark of Hodgkin lymphoma cells, stimulate proliferation and synergize with NF-κB," European Molecular Biology Organization Journal, 21:4104-4113 (2002).
Monti et al., "Molecular profiling of diffuse large B-cell lymphoma identifies robust subtypes including one characterized by host inflammatory response," Blood, 105(5):1851-1861 (2005).
Perillo et al., "Apoptosis of T cells mediated by galectin-1," Nature, 378:(6558)736-739 (1995).
Polo et al., "Transcriptional signature with differential expression of BCL6 target genes accurately identifies BCL6-dependent diffuse large B cell lymphomas," PNAS, 104(9):3207-3212 (2007).
Rabinovich, GA, "Galectin-1 as a potential cancer target," British Journal of Cancer, 92:1188-1192 (2005).
Rabinovich et al., "Galectins and their ligands: amplifiers, silencers or tuners of the inflammatory response?," Trends Immunol., 23(6):313-320 (2002).
Rabinovich et al., "Recombinant Galectin-1 and Its Genetic Delivery Suppress Collagen-induced Arthritis via T Cell Apoptosis," J. Exp. Med., 190(3):385-397 (1999).
Re et al., "Molecular pathogenesis of Hodgkin's lymphoma," J. Clin. Oncol., 23(26):6379-6386 (2005).
Reiner et al., "Identifying differentially expressed genes using false discovery rate controlling procedures," Bioinformatics, 19(3):368-375 (2003).
Rodig et al., "TRAF1 expression and c-Rel activation are useful adjuncts in distinguishing classical Hodgkin lymphoma from a subset of morphologically or immunophenotypically similar lymphomas," Am. J. Surg. Pathol., 29(2):196-203 (2005).
Rubinstein et al., "Targeted inhibition of galectin-1 gene expression in tumor cells results in heightened T cell-mediated rejection; A potential mechanism of tumor-immune privilege," Cancer Cell, 5(3):241-251 (2004).
Salvatore et al., "High resolution methylation analysis of the galectin-1 gene promoter region in expressing and nonexpressing tissues," FEBS Lett., 421(2):152-158 (1998).
Santucci et al., "Galectin-1 suppresses experimental colitis in mice," Gastroenterology, 124(5):1381-1394 (2003).
Savage et al., "The molecular signature of mediastinal large B-cell lymphoma differs from that of other diffuse large B-cell lymphomas and shares features with classical Hodgkin lymphoma," Blood, 102(12):3871-3879 (2003).
Scherf et al., "Highly specific localization of promoter regions in large genomic sequences by Promoterinspector: a novel context analysis approach," J. Mol. Biol., 297(3):599-606 (2000).
Schwering et al., "Loss of the B-lineage-specific gene expression program in Hodgkin and Reed-Sternberg cells of Hodgkin lymphoma," Blood, 101(4):1505-1512 (2003).
Skinnider et al., "The role of interleukin 13 in classical Hodgkin lymphoma," Leuk. Lymphoma, 43(6):1203-1210 (2002).
Smith et al., "The phosphodiesterase PDE4B limits cAMP-associated PI3K/AKT-dependent apoptosis in diffuse large B-cell lymphoma," Blood, 105(1):308-316 (2005).
Stillman et al., "Galectin-3 and Galectin-1 Bind Distinct Cell Surface Glycoprotein Receptors to Induce T Cell Death," The Journal of Immunology, 176:778-789 (2006).
Thijssen et al., "Galectic-1 is essential in tumor angiogenesis and is a target for antiangiogenesis therapy," PNAS, 103(43):15975-15980 (2006).

(56) References Cited

OTHER PUBLICATIONS

Toscano et al., "Differential glycosylation of TH1, TH2 and TH-17 effector cells selectively regulates susceptibility to cell death," Nat. Immunol., 8(8):825-834 (2007).

Toscano et al., "Dissecting the pathophysiologic role of endogenous lectins: glycan-binding proteins with cytokine-like activity?," Cytokine Growth Factor Rev., 18(1-2):57-71 (2007).

Toscano et al., "Galectin-1 Suppresses Autoimmune Retinal Disease by Promoting Concomitant Th2- and T Regulatory-Mediated Anti-Inflammatory Response," The Journal of Immunology, 176:6323-6332 (2006).

van der Leij et al., "Strongly enhanced IL-10 production using stable galectin-1 homodimers," Mol. Immunol., 44:506-513 (2007).

Vasta et al., "Structural and functional diversity of lectin repertoires in invertebrates, protochordates and ectothermic vertebrates," Curr. Opin. Struct. Biol., 14(5):617-630 (2004).

von Wasielewski et al., "Tissue eosinophilia correlates strongly with poor prognosis in nodular sclerosing Hodgkin's disease, allowing for known prognostic factors," Blood, 95(4):1207-1213 (2000).

Yuan et al., "siRNA Selection Server: an automated siRNA oligonucleotide prediction server," Nucleic Acids Research, 32:W130-W134 (2004).

Zorn et al., "IL-2 regulates *FOXP3* expression in human CD4+CD25+ regulatory T cells through a STAT-dependent mechanism and induces the expansion of these cells in vivo," Blood, 108(5):1571-1579 (2006).

Cho et al., "Galectin-1, a β-Galactoside-binding Lectin in Chinese Hamster Ovary Cells," The Journal of Biological Chemistry, 270(10):5198-5206 (1995).

Gajl-Peczalska et al., "B and T cell lymphomas. Analysis of blood and lymph nodes in 87 patients," Am. J. Med., 59(5):674-685 (1975) Abstract.

* cited by examiner

COMPOSITIONS, KITS, AND METHODS FOR THE MODULATION OF IMMUNE RESPONSES USING GALECTIN-1

RELATED APPLICATIONS

This application claims the benefit of U.S. Provisional Application Ser. No. 60/959,830, filed on Jul. 17, 2007; the entire contents of the application is incorporated herein by reference.

BACKGROUND OF THE INVENTION

Classical Hodgkin lymphoma (cHL) is a B-cell malignancy diagnosed in approximately 20,000 new patients in North America and Europe each year; over 90% of these patients are young adults. Classical HLs include small numbers of malignant Reed-Sternberg (RS) cells within an extensive inflammatory infiltrate (Re et al. (2005) *J Clin Oncol* 23:6379-6386) which includes abundant T helper (Th)-2 and T regulatory ($T_{reg}$) cells. The tumor cells derive from pre-apoptotic germinal center B cells that have undergone crippling mutations of their rearranged immunoglobulin genes (Re et al. (2005) *J Clin Oncol* 23:6379-6386; Kanzler et al. (1996) *J Exp Med* 184:1495-1505). Classical HL RS cells lack B-cell receptor-mediated signals and rely on alternative survival and proliferation pathways activated by transcription factors such as NF-κB and AP1 (Mathas et al. (2002) *EMBO J.* 21: 4104-4113; Kuppers et al. (2002) *Ann Oncol* 13:11-18; Schwering et al. (2003) *Blood* 101:1505-1512). In cHL, the tumor cells exhibit constitutive AP1 activation, express high levels of the AP1 components, cJUN and JUNB, and depend upon AP1-mediated proliferation signals (Mathas et al. (2002) *EMBO J.* 21: 4104-4113).

Although primary cHLs have a brisk inflammatory infiltrate, there is little evidence of an effective host anti-tumor immune response. The reactive T-cell population includes predominantly Th2-type and $CD4^+$ $CD25^{high}$ $FOXP3^+$ $T_{reg}$ cells that directly suppress immune responses and protect cHL RS cells from immune attack (Re et al. (2005) *J Clin Oncol* 23:6379-6386; Marshall et al. (2004) *Blood* 103:1755-1762; Gandhi et al. (2006) *Blood* 108:2280-2289, Ishida et al. (2006) *Cancer Res* 66:5716-5722); Th1, NK and cytotoxic T cells are markedly under-represented. In addition, primary cHLs are characterized by a unique cytokine and chemokine profile, including IL-4, IL-5, IL-10 and IL-13 (Re et al. (2005) *J Clin Oncol* 23:6379-6386; Skinnider et al. (2002) *Leuk Lymphoma* 43:1203-1210). In fact, IL-13 is a critical growth factor for cHL RS cells (Re et al. (2005) *J Clin Oncol* 23:6379-6386; Skinnider et al. (2002) *Leuk Lymphoma* 43:1203-1210). However, the molecular signals and endogenous factors responsible for creating and maintaining the Th2-skewed immunosuppressive microenvironment in cHL remain to be defined.

Galectins have recently emerged as novel regulators of immune cell homeostasis, and tumor immune escape (Rabinovich et al. (2002) *Trends Immunol* 23:313-320; Liu and Rabinovich (2005) *Nature Reviews Cancer* 5:29-41; Rubinstein et al. (2004) *Cancer Cell* 5:241-251; Le et al. (2005) *J Clin Oncol* 23:8932-8941). Galectin-1 (Gal1), an evolutionarily conserved member of this family (Vasta et al. (2004) *Curr Opin Struct Biol* 14:617-630), preferentially recognizes multiple Gal β1,4 GlcNAc (LacNAc) units which may be presented on the branches of N- or O-linked glycans on cell surface glycoproteins such as CD45, CD43 and CD7 (Stillman et al. (2006) *J Immunol* 176:778-789). Through binding and crosslinking of specific glycoconjugates, Gal1 has the potential to inhibit T-cell effector functions and regulate the inflammatory response (Perillo et al. (1995) *Nature* 378:736-739; Rabinovich et al. (1999) *J Exp Med* 190:385-397; Toscano et al. (2006) *J Immunol* 176:6323-6332; Santucci et al. (2003) *Gastroenterol* 124: 1381-1394; Baum et al. (2003) *Clin Immunol* 109:295-307). In several murine models of chronic inflammatory diseases, recombinant Gal1 suppressed Th1-dependent responses and increased T-cell susceptibility to activation-induced cell death (Rabinovich et al. (1999) *J Exp Med* 190:385-397; Toscano et al. (2006) *J Immunol* 176:6323-6332; Santucci et al. (2003) *Gastroenterol* 124: 1381-1394; Baum et al. (2003) *Clin Immunol* 109: 295-307).

In a recently described solid tumor (murine melanoma) model, Gal1 was also found to play a pivotal role in promoting escape from T-cell-dependent immunity and conferring immune privilege to tumor cells (Rubinstein et al. (2004) *Cancer Cell* 5:241-251). In this model, Gal1 blockade markedly enhanced syngeneic tumor rejection and tumor-specific T-cell-mediated immune responses (Rubinstein et al. (2004) *Cancer Cell* 5:241-251). In another recently described solid tumor (head and neck squamous cell carcinomas), Gal1 overexpression was inversely correlated with the number of infiltrating T cells and was an independent prognostic factor for shorter overall survival (Le et al. (2005) *J Clin Oncol* 23:8932-8941). WO2006/108474 describes the use of RNAi molecules for the treatment of cancer and non-Hodgkin's lymphoma.

In view of the above, it is clear that there remains a need in the art for compositions and methods to combat immune disorders, including Hodgkin lymphoma. The present invention relates in general to a role of Gal1 in immune disorders, including Hodgkin lymphoma.

SUMMARY OF THE INVENTION

The present invention is based, in part, on the discovery that galectin-1 (Gal1) plays a role in immune disorders, including Hodgkin lymphoma. Accordingly, in one aspect, the invention provides for a method for modulating an immune response by modulating the interaction between a Gal1 polypeptide or a fragment thereof and its natural binding partner(s). In one embodiment, the method includes contacting an immune cell with an agent that modulates the interaction between a Gal1 polypeptide or a fragment thereof and its natural binding partner(s) to thereby modulate the immune response. In another embodiment, the immune response is upregulated or downregulated. In yet another embodiment, signaling via the Gal1 binding partner is inhibited using an agent, e.g., a blocking antibody or an antigen binding fragment thereof that recognizes a Gal1 polypeptide or a fragment thereof and a blocking antibody, an antigen binding fragment thereof that recognizes the Gal1 binding partner(s) or a fragment thereof, or an RNA interference molecule that downregulates Gal1. In still another embodiment, the immune cell is contacted with an additional agent that upregulates an immune response. In other embodiments, the step of contacting occurs in vivo or in vitro.

In another aspect, the invention provides for a method for treating a subject having a condition that would benefit from upregulation of an immune response. In one embodiment, the method includes administering an agent, e.g., a blocking antibody or an antigen binding fragment thereof that recognizes a Gal1 polypeptide or a fragment thereof, a blocking antibody or an antigen binding fragment thereof that recognizes the Gal1 binding partner(s) or a fragment thereof, or an RNA interference molecule that downregulates Gal1, that inhibits the interaction between a Gal1 polypeptide or a fragment thereof and its natural binding partner(s) or a fragment thereof on cells of a subject such that a condition that would benefit from upregulation of an immune response is treated. In another embodiment, the method further comprises administering a second agent that upregulates an immune response to the subject. In yet another embodiment, the method further comprises administering a combination treatment, e.g., chemotherapy treatment. In a further embodiment, the subject is a human. In yet a further embodiment, the human has Hodgkin lymphoma.

In another aspect, the invention features a method for detecting a Gal1 polypeptide or nucleic acid or fragments thereof in a sample. In one embodiment, the method includes contacting the sample with a compound which selectively binds to a Gal1 polypeptide or fragment thereof and determining whether the compound binds to a Gal1 polypeptide or fragment thereof in the sample to thereby detect the presence of a Gal1 polypeptide or fragment thereof. In one embodiment, the compound which binds to the polypeptide is an antibody. In another aspect, the method includes contacting a sample with a nucleic acid probe or primer which selectively hybridizes to a Gal1 polynucleotide or fragment thereof and determining whether the nucleic acid probe or primer binds to a nucleic acid molecule in the sample to thereby detect the presence of a Gal1 polynucleotide or fragment thereof. In yet another embodiment, the sample comprises mRNA molecules and is contacted with a nucleic acid probe.

In yet another aspect, the invention provides a method for identifying a compound which binds to a Gal1 polypeptide or fragment thereof. In one such embodiment, the method includes contacting a Gal1 polypeptide or fragment thereof, or a cell expressing said polypeptide with a test compound and determining whether said polypeptide binds to the test compound. In another embodiment, the binding of the test compound to a Gal1 polypeptide or fragment thereof is detected by several methods, including detection of binding by direct detection of test compound/polypeptide binding, detection of binding using a competition binding assay, and detection of binding using an assay for Gal1 activity.

In still another aspect, the invention provides for a method for modulating the activity of a Gal1 polypeptide or fragment thereof. In one embodiment, the method includes contacting the polypeptide or a cell expressing the polypeptide with a compound which binds to the polypeptide in a sufficient concentration to modulate the activity of the polypeptide.

In a further aspect, the invention provides for a method for identifying a compound which modulates the activity of a Gal1 polypeptide or fragment thereof. In one embodiment, the method includes contacting a Gal1 polypeptide or fragment thereof with a test compound and determining the effect of the test compound on the activity of the polypeptide to thereby identify a compound which modulates the activity of the polypeptide.

In still another aspect, the invention provides for a cell-based assay for screening for compounds which modulate the activity of Gal1. In one embodiment, the assay includes contacting a cell expressing a Gal1 binding partner(s) or fragment(s) thereof with a test compound and determining the ability of the test compound to modulate the activity of the Gal1 binding partner(s) or fragment(s) thereof. In another embodiment, the cell(s) are isolated from an animal model of an immune disorder, e.g., a Hodgkin lymphoma animal model. In another embodiment, the cell(s) are isolated from a cell line associated with an immune disorder, e.g., Hodgkin lymphoma cell line. In yet another embodiment, the cell(s) are isolated from a subject suffering from an immune disorder, e.g., Hodgkin lymphoma.

In yet another aspect, the invention provides for a cell-free assay for screening for compounds which modulate the binding of Gal1 or fragment thereof to a Gal1 binding partner(s) or fragment(s) thereof. In one embodiment, the assay includes contacting a Gal1 polypeptide or fragment thereof with a test compound and determining the ability of the test compound to bind to the Gal1 polypeptide or fragment thereof.

In one aspect, the invention provides for a method of assessing whether a subject has a condition, e.g., an immune disorder, including cancer, e.g., Hodgkin lymphoma, that would benefit from upregulation of an immune response. In one embodiment, the method includes comparing the level of expression of Gal1 in a subject sample and the normal level of expression of Gal1 in a control sample, wherein a significant increase in the level of expression of Gal1 in the subject sample relative to the normal level is an indication that the subject is afflicted with a condition. In another embodiment, the sample comprises cells obtained from the subject, for example, cells in fluid (e.g., whole blood fluid, serum fluid, plasma fluid, interstitial fluid, cerebrospinal fluid, lymph fluid, saliva, stool, and urine). In another embodiment, the level of expression of Gal1 is assessed by detecting the presence in the samples of a protein encoded by a Gal1 polynucleotide or a polypeptide or protein fragment thereof comprising the protein. For example, the presence of the protein can be detected using a reagent which specifically binds to the protein, e.g., an antibody, an antibody derivative, or an antibody fragment. In another embodiment, the level of expression of Gal1 is assessed by detecting the presence in the sample of a transcribed polynucleotide encoded by a Gal1 polynucleotide or a portion of the transcribed polynucleotide, e.g., mRNA or cDNA. For example, the presence of the polynucleotide can be assayed by detecting the presence in the sample of a transcribed polynucleotide which anneals with a Gal1 polynucleotide or anneals with a portion of a Gal1 polynucleotide, under stringent hybridization conditions. In another embodiment, the transcribed polynucleotide to be detected can be amplified. In still another embodiment, a significant increase between the level of expression of Gal1 in the subject sample relative to the normal level of expression of Gal1 in the sample from the control subject can be at least about two, three, four, five, six, seven, eight, nine, ten, twenty or more fold greater.

In another aspect, the invention provides for a method for monitoring the progression of an immune disorder, e.g., Hodgkin lymphoma, in a subject. In one embodiment, the method includes detecting in a subject sample at a first point in time the expression of Gal1, repeating the previous step at a subsequent point in time, and comparing the level of expression of Gal1 detected at each point in time to monitor the progression of the immune disorder. In another embodiment, the subject can undergo treatment to ameliorate the immune disorder between the first point in time and the subsequent point in time. In one embodiment, the treatment may be chemotherapy. In yet another embodiment, the chemotherapy treatment may be combined with an agent.

In another aspect, the invention provides for a method for assessing the efficacy of a test compound for inhibiting an immune disorder, e.g., Hodgkin lymphoma, in a subject. In one embodiment, the method includes comparing the level of expression of Gal1 in a first sample obtained from the subject and exposed to the test compound and the level of expression of Gal1 in a second sample obtained from the subject, wherein the second sample is not exposed to the test compound, and a significantly lower level of expression of Gal1, relative to the second sample, is an indication that the test compound is efficacious for inhibiting an immune disorder in the subject. In another embodiment, the first and second samples can be portions of a single sample obtained from the subject or portions of pooled samples obtained from the subject. In yet another embodiment, the method further comprises administering a combination treatment, wherein the treatment may include chemotherapy.

In another aspect, the invention provides for a method for predicting the clinical outcome of a patient with an immune disorder, e.g., Hodgkin lymphoma. In one embodiment, the method includes determining the level of expression of Gal1 in a patient sample, determining the level of expression of Gal1 in a sample from a control subject having a good clinical outcome, and comparing the level of expression of Gal1 in the patient sample and in the sample from the control subject, wherein a significantly higher level of expression in the patient sample as compared to the expression level in the sample from the control subject is an indication that the patient has a poor clinical outcome.

In another aspect, the invention provides for a method of assessing the efficacy of a therapy for inhibiting an immune disorder, e.g., Hodgkin lymphoma, in a subject. In one embodiment, the method includes comparing the level of expression of Gal1 in the first sample obtained from the subject prior to providing at least a portion of the therapy to the subject and the level of expression of Gal1 in a second sample obtained from the subject following provision of the portion of the therapy, wherein a significantly lower level of expression of Gal1 in the second sample, relative to the first sample, is an indication that the therapy is efficacious for inhibiting the immune disorder, e.g., Hodgkin lymphoma, in the subject.

In another aspect, the invention provides for methods of making antibodies that specifically bind to a Gal1 polypeptide or a fragment thereof. In one embodiment, the method involves making an isolated hybridoma and includes immunizing a mammal using a composition comprising a Gal1 polypeptide or a fragment thereof, isolating splenocytes from the immunized mammal, fusing the isolated splenocytes with an immortalized cell line to form hybridomas, and screening individual hybridomas for production of an antibody which specifically binds with the polypeptide thereof to isolate the hybridoma. In another embodiment, the antibody or antigen binding fragment thereof produced by the hybridoma can be used to specifically recognize Gal1 polypeptide or a fragment thereof. In still another embodiment, antibodies that specifically bind to a Gal1 polypeptide or a fragment thereof can be made by immunizing a mammal with an effective amount of a preparation of a material comprising a Gal1 polypeptide or a fragment thereof, in combination with an adjuvant.

In another aspect, the invention provides for novel compositions of matter that may be used in the methods of the invention. In one embodiment, the invention provides antibodies or antigen binding fragment thereof that specifically bind to a Gal1 polypeptide or a fragment thereof. In one embodiment, the antibodies or antigen binding fragment thereof can bind to a fragment of human Gal1, a polypeptide which is encoded by a nucleic acid comprising a nucleotide sequence which is at least 80% homologous to a nucleic acid comprising the nucleotide sequence human Gal1, or a polypeptide comprising an amino acid sequence which is at least 80% homologous to the amino acid sequence of human Gal1. In other embodiments, the antibodies or antigen binding portions thereof can be monoclonal, polyclonal, chimeric, or humanized. In another embodiment, the antibodies or antigen binding portions thereof can be detectably labeled. Non-limiting examples of detectable labels include an enzyme, a prosthetic group, a fluorescent material, a luminescent material, a bioluminescent material, and a radioactive material. In other embodiments, the antibodies or antigen binding portions thereof inhibit Hodgkin lymphoma in a subject. In yet another embodiment, the antibodies or antigen binding portions thereof specifically bind a Gal1 epitope comprising the ligand-specific carbohydrate binding domain or fragment thereof, e.g., amino acids 30 to 90 of human Gal1 or amino acids 62 to 86 of human Gal1. In another embodiment, the antibodies or antigen binding portion thereof can comprise an effector domain and/or an Fc domain. In yet another embodiment, the antibodies or antigen binding portion thereof can be single-chain antibodies and/or Fab fragments. In still another embodiment, a pharmaceutical composition comprising the antibodies or antigen binding portion thereof in a pharmaceutically acceptable carrier are provided.

In another aspect, the invention provides RNA interference compositions and methods useful for the downregulation of Gal1 expression levels. In one embodiment, an RNA interference molecule suitable for reducing the expression of Gal1 comprises the sequence, GCTGCCAGATGGATACGAA (SEQ ID NO: 1), or a fragment or derivative thereof. In another embodiment, an expression vector (e.g., an expression vector suitable for the production of double stranded RNA) comprises the sequence, GCTGCCAGATGGATAC-GAA (SEQ ID NO: 1), or a fragment or derivative thereof are provided. In another embodiment, the RNA interference compositions can be used to treat an immune disorder, e.g., Hodgkin lymphoma.

In still another aspect, the invention provides for various kits, which may include the novel compositions described herein. In one embodiment, a kit is provided that comprises an agent which selectively binds to a Gal1 polypeptide or fragment thereof and instructions for use. In another embodiment, a kit is provided that comprises an agent which selectively hybridizes to a Gal1 polynucleotide or fragment thereof and instructions for use. In yet another embodiment, the agent which selectively hybridizes to a Gal1 polynucleotide or fragment thereof is an RNA interference molecule.

In yet another aspect, the invention provides for a vaccine comprising an antigen and an agent that inhibits the interaction between Gal1 or fragment thereof and its natural binding partner(s) or fragment(s) thereof.

BRIEF DESCRIPTION OF THE DRAWINGS

In FIG. 1A, the Gal1 expression profiles of DLBCL, MLBCL and cHL cell lines are shown. The color scale at the bottom of the figure indicates relative expression and standard deviations from the mean. Red connotes high-level expression, while blue indicates low-level expression. In FIG. 1B, the plots represent the median expression of Gal1 (boxes) in LBCL versus cHL cell lines±25-75 percentile (bars) and ±range (whiskers). In FIG. 1C, the respective cHL cell lines (KMHZ, HDLM2, SupHD1, L1236, L540, L428, HD-MY-Z), the MLBCL cell line (Karpas 1106) and DLBCL cell lines (all others) are indicated. FIG. 1D shows immunohistochemical (IHC) analyses of Gal1 in representative primary cHL (top panels) and DLBCL (bottom panels) cells (original magnification 40× and 400×, respectively).

FIG. 2A shows the results of analyses of the AP1-dependent Gal1 enhancer. The previously described Gal1 promoter (Salvatore et al. (1998) *FEBS Lett* 421:152-8) and putative enhancer element including or lacking the predicted AP1 binding site (represented by a black bar) were cloned into a luciferase reporter vector, transiently transfected into cHL HD-MY-Z cells and assayed for luciferase activities. Representative luciferase activities from three independent experiments are normalized to *Renilla* luciferase activity and presented as bars±standard deviations. FIG. 2B shows results of the selective activity of the Gal1 enhancer. Classical HL, DLBCL and fibroblast cell lines were transfected with either the Gal1 promoter-only vector (pGL3-Gal1$_{-403+67}$-Luc) or the promoter-enhancer construct (pGL3-Gal1$_{403+67}$-Luc-e$_{1346+1746}$) and assessed as in FIG. 2A for their respective luciferase activities. FIG. 2C shows that the Gal1 enhancer is dependent on AP-1 using electrophoretic mobility shift assays. Nuclear extracts from DLBCL cell lines (DHL4, DHL7 and Toledo) or cHL cell lines (HD-MY-Z, L428 and SupHD1) were incubated with wild type (WT) or mutant (MUT) $^{32}$P labeled, double-stranded DNA probe corresponding to an AP1 binding site in the Gal1 enhancer. Specific, unlabeled competitor and antibodies against cJun or β-actin (control) were included in certain assays as indicated. The gel-shift band corresponding to probe-protein complex is indicated with an arrow and super-shift bands corresponding to probe-protein-antibody complex are noted with asterisks. FIG. 2D shows that the Gal1 enhancer is dependent on cJUN. HD-MY-Z cells were cotransfected with the Gal1 promoter-only vector or the Gal1 promoter-enhancer construct with either the dominant-negative cJUN (cJUN-DN) construct (cJUN-DN) or empty vector. Luciferase activities were determined as in FIG. 2A. FIG. 2E shows that inhibition of AP1 decreases Gal1 transcript abundance. HD-MY-Z cells were transfected with either the dominant-negative cJUN construct (cJUN-DN) or empty vector and relative Gal1 mRNA abundance was then assessed by RQ-PCR.

FIG. 3A shows that Gal1 expression can be blocked in the cHL HD-MY-Z cell line using RNA interference (RNAi). HD-MY-Z cells were transduced with pSI-REN-RetroQ vector encoding Gal1-specific shRNA (Gal1 shRNA, denoted as "G") or scrambled control shRNA (SCR shRNA, denoted as "S") and analyzed thereafter for Gal1 protein expression. FIG. 3B shows viability of total (CD3$^+$) and CD4$^+$ T cells co-cultured with Gal1 shRNA cHL or control SCR shRNA cHL cells. Following co-culture, T-cell viability was assessed using 3-color Annexin-V, -CD3 and -CD4 flow cytometry. FIG. 3C shows the relative abundance of the Th1- and Th2-specific transcription factors, Tbet and GATA3, in CD4$^+$ cells from the Gal1 shRNA and SCR shRNA (control) cHL/T-cell co-cultures presented in FIG. 3B.

DETAILED DESCRIPTION OF THE INVENTION

Figure 1:
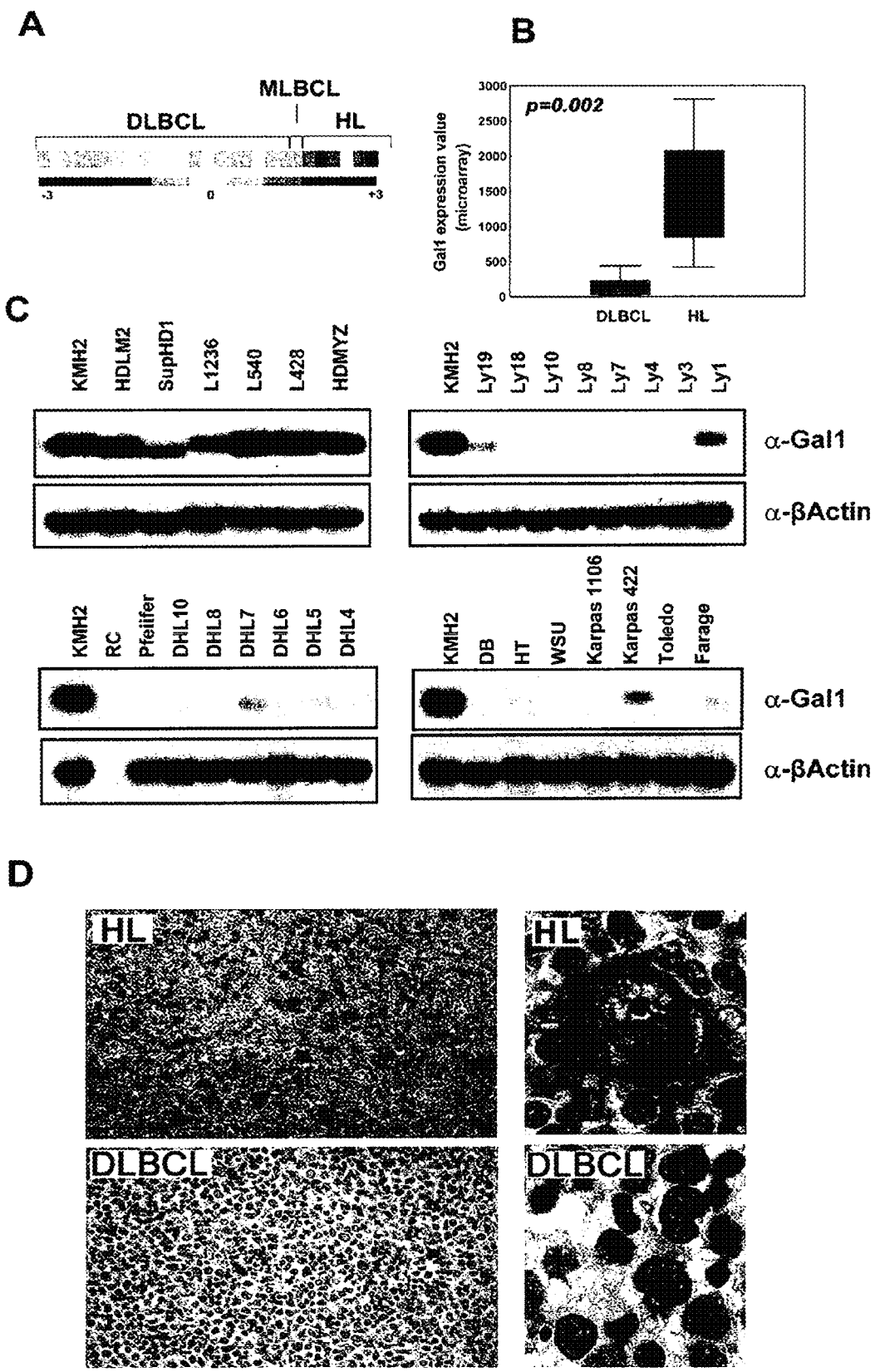
FIGS. 1A-1D shows that Gal1 is overexpressed in classical Hodgkin lymphoma (cHL) cell lines and primary tumors. Relative Gal1 mRNA abundance (FIG. 1A and FIG. 1B) and protein expression (FIG. 1C) in a panel of LBCL and cHL cell lines is depicted.

The invention is based, in part, on the discovery that galectin-1 (Gal1) is overexpressed by Reed-Sternberg (RS) cells associated with classical Hodgkin lymphomas (cHLs) and that the Gal1 overexpression by RS cells is directly implicated in the development and maintenance of an immunosuppressive Th2/T$_{reg}$-skewed microenvironment in cHL leading to an ineffective host anti-tumor immune response. Thus, agents such as natural ligands, derivatives of natural ligands, and small molecules, RNA interference, aptamer, peptides, peptidomimetics, and antibodies that specifically bind to the Gal1 gene or gene products, or fragments thereof, can be utilized to modulate, e.g., increase, immune surveillance in immune disorders, e.g., Hodgkin lymphoma. Additionally, agents such as Gal1 gene sequences, Gal1 gene products, anti-Gal1 RNA interference molecules, anti-Gal1 antibodies (i.e., antibodies that specifically bind to Gal1 gene products or fragments thereof), or fragments thereof, can be utilized to reduce the level of TH2 cell activity and/or increase the level of TH1 cell activity to restore immune surveillance in immune disorders, e.g., Hodgkin lymphoma.

Thus, it has been discovered that a higher than normal level of expression of Gal1 correlates with the presence of an immune disorder, e.g., Hodgkin lymphoma, in a patient. Gal1 polypeptides and fragments thereof, e.g., biologically active or antigenic fragments thereof, are provided, as reagents or targets in assays applicable to treatment and/or diagnosis of immune disorders, e.g., Hodgkin lymphoma. In particular, the methods and compositions of the present invention relate to detection and/or modulation of expression and/or activity of a Gal1 gene or fragment thereof, e.g., biologically active fragments thereof, as well as to the detection and/or modulation of expression and/or activity of gene products or fragments thereof encoded by the Gal1 gene, e.g., biologically active fragments thereof. The methods and compositions of the present invention can utilize the Gal1 gene or gene sequence or fragments thereof, as well as gene products of the Gal1 gene and/or modulators thereof or fragments thereof, e.g., antibodies which specifically bind to such Gal1 gene products.

In one aspect, methods are provided for detecting the presence, absence, stage, and other characteristics of immune disorders, e.g., Hodgkin lymphoma, in a sample that are relevant to prevention, diagnosis, characterization, and therapy in a patient.

The invention also features compositions of matter, including antibodies (e.g., antibodies which specifically bind to any one of the polypeptides described herein) as well as fusion polypeptides, including all or a fragment of a polypeptide described herein. In addition, the invention features compositions useful for the reduction of Gal1 nucleic acids (e.g., Gal1 mRNA or hnRNA or fragments thereof), including RNA interference compositions, directed against Gal1 nucleic acids or fragments thereof.

I. Definitions

The articles "a" and "an" are used herein to refer to one or to more than one (i.e. to at least one) of the grammatical object of the article. By way of example, "an element" means one element or more than one element.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., Gal1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, *Nature Biotechnology* 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to Gal1 polypeptides or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune disorder" includes immune diseases, conditions, and predispositions to, including, but not limited to, Hodgkin lymphoma (including, e.g., lymphocyte-rich classical Hodgkin lymphoma, mixed cellularity classical Hodgkin lymphoma, lymphocyte-depleted classical Hodgkin lymphoma, nodular sclerosis classical Hodgkin lymphoma, and nodular lymphocyte predominant Hodgkin lymphoma), cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy).

As used herein, the term "immune response" includes T cell mediated and/or B cell mediated immune responses. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "inhibit" includes the decrease, limitation, or blockage, of, for example a particular action, function, or interaction.

As used herein, the term "interaction", when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

As used herein, an "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

An "isolated antibody", as used herein, is intended to refer to an antibody that is substantially free of other antibodies having different antigenic specificities (e.g., an isolated antibody that specifically binds Gal1 polypeptide or a fragment thereof is substantially free of antibodies that specifically bind antigens other than a Gal1 polypeptide or a fragment thereof). Moreover, an isolated antibody may be substantially free of other cellular material and/or chemicals.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of Gal1 polypeptide or fragment thereof, in which the protein is separated from cellular components of the cells from which it is isolated or recombinantly produced. In one embodiment, the language "substantially free of cellular material" includes preparations of Gal1 protein or fragment thereof, having less than about 30% (by dry weight) of non-Gal1 protein (also referred to herein as a "contaminating protein"), more preferably less than about 20% of non-Gal1 protein, still more preferably less than about 10% of non-Gal1 protein, and most preferably less than about 5% non-Gal1 protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe, for specifically detecting the expression of a marker of the invention. The kit may be promoted, distributed, or sold as a unit for performing the methods of the present invention.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the invention. A marker protein comprises the entire or a partial sequence of any of the sequences set forth in the Sequence Listing. The terms "protein" and "polypeptide" are used interchangeably.

As used herein, the term "modulate" includes up-regulation and down-regulation, e.g., enhancing or inhibiting a response.

The "normal" level of expression of a marker is the level of expression of the marker in cells of a subject, e.g., a human patient, not afflicted with an immune disorder, e.g., Hodgkin lymphoma. An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples. A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, "subject" refers to any healthy animal, mammal or human, or any animal, mammal or human afflicted with an immune disorder, e.g., Hodgkin lymphoma. The term "subject" is interchangeable with "patient".

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

I. Description

The present invention relates to methods and compositions for the treatment and diagnosis of immune disorders, especially T lymphocyte-related disorders, including, but not limited to, Hodgkin lymphoma (including, e.g., lymphocyte-rich classical Hodgkin lymphoma, mixed cellularity classical Hodgkin lymphoma, lymphocyte-depleted classical Hodgkin lymphoma, nodular sclerosis classical Hodgkin lymphoma, and nodular lymphocyte predominant Hodgkin lymphoma), cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy).

In particular, the methods and compositions of the present invention relate to detection and/or modulation of expression and/or activity of a gene referred to herein as the galectin-1 (Gal1) gene or a fragment thereof, e.g., a biologically active fragment thereof, as well as to the detection and/or modulation of expression and/or activity of gene products encoded by the Gal1 gene (i.e., a "Gal1 gene product") or fragments thereof, e.g., biologically active fragments thereof. The methods and compositions of the present invention can utilize the Gal1 gene or gene sequence or fragments thereof, as well as gene products of the Gal1 gene and/or modulators thereof, e.g., antibodies which specifically bind to such Gal1 gene products, or fragments thereof. Sequences, structures, domains, biophysical characteristics, and functions of Gal1 gene and gene products have been described in the art. See, for example, Rabinovich et al. (2002) *Trends Immunol* 23:313-320; Liu and Rabinovich (2005) *Nature Reviews Cancer* 5:29-41; Rubinstein et al. (2004) *Cancer Cell* 5:241-251; Le et al. (2005) *J Clin Oncol* 23:8932-8941; Vasta et al. (2004) *Curr Opin Struct Biol* 14:617-630; Toscano et al. (2007) *Cyt Growth Fact Rev* 18:57-71; Camby et al. (2006) *Glycobiol* 16:137R-157R, each of which is incorporated herein, by reference, in its entirety. Gal1 gene and gene products from many species are known and include, for example, chimpanzee Gal1 (NCBI Accession XM_001162066), rat Gal1 (NCBI Accession NM_019904), mouse Gal1 (NM_008495), and chicken Gal1 (NM_205495). Human Gal1 sequences include those listed below.

```
Gal1 coding nucleic acid sequence:
                                (SEQ ID NO: 2)
ATGGCTTGTG GTCTGGTCGC CAGCAACCTG AATCTCAAAC

CTGGAGAGTG CCTTCGAGTG CGAGGCGAGG TGGCTCCTGA

CGCTAAGAGC TTCGTGCTGA ACCTGGGCAA AGACAGCAAC
```

```
                AACCTGTGCC TGCACTTCAA CCCTCGCTTC AACGCCCACG

GCGACGCCAA CACCATCGTG TGCAACAGCA AGGACGGCGG

GGCCTGGGGG ACCGAGCAGC GGGAGGCTGT CTTTCCCTTC

CAGCCTGGAA GTGTTGCAGA GGTGTGCATC ACCTTCGACC

AGGCCAACCT GACCGTCAAG CTGCCAGATG GATACGAATT

CAAGTTCCCC AACCGCCTCA ACCTGGAGGC CATCAACTAC

ATGGCAGCTG ACGGTGACTT CAAGATCAAA TGTGTGGCCT

TTGACTGA

Gal1 protein sequence:
                                                     (SEQ ID NO: 3)
                MACGLVASNL NLKPGECLRV RGEVAPDAKS FVLNLGKDSN

NLCLHFNPRF NAHGDANTIV CNSKDGGAWG TEQREAVFPF

QPGSVAEVCI TFDQANLTVK LPDGYEFKFP NRLNLEAINY

MAADGDFKIK CVAFD
```

The invention is based, in part, on the discovery that Gal1 is overexpressed by Reed-Sternberg (RS) cells associated with classical Hodgkin lymphomas (cHLs) and that the Gal1 overexpression by RS cells is directly implicated in the development and maintenance of an immunosuppressive Th2/$T_{reg}$-skewed microenvironment in cHL leading to an ineffective host anti-tumor immune response. Thus, agents such as natural ligands, derivatives of natural ligands, and small molecules, RNA interference, aptamer, peptides, peptidomimetics, and antibodies that specifically bind to the Gal1 gene or gene products or fragments thereof can be utilized to modulate (e.g., increase) immune surveillance in immune disorders, e.g., Hodgkin lymphoma. Additionally, agents such as Gal1 gene sequences, Gal1 gene products, anti-Gal1 RNA interference molecules, anti-Gal1 antibodies (i.e., antibodies that specifically bind to Gal1 gene products), or fragments thereof, can be utilized to reduce the level of TH2 cell activity and/or increase the level of TH1 cell activity to restore immune surveillance in immune disorders, e.g., Hodgkin lymphoma.

The Gal1 gene is also expressed in other cells known in the art. See, for example, Rabinovich et al. (2002) *Trends Immunol* 23:313-320; Liu and Rabinovich (2005) *Nature Reviews Cancer* 5:29-41; Rubinstein et al. (2004) *Cancer Cell* 5:241-251; Le et al. (2005) *J Clin Oncol* 23:8932-8941; Vasta et al. (2004) *Curr Opin Struct Biol* 14:617-630; Toscano et al. (2007) *Cyt Growth Fact Rev* 18:57-71; Camby et al. (2006) *Glycobiol* 16:137R-157R, each of which is incorporated herein, by reference, in its entirety. Thus, the above-described compositions (e.g., natural ligands, derivatives of natural ligands, and small molecules, RNA interference, aptamer, peptides, peptidomimetics, antibodies that specifically bind to the Gal1 gene or gene products, or fragments thereof) can also be utilized to modulate immune responses in these immune related cell. Additional studies indicate that Gal1 is also overexpressed in other hematologic malignancies, including certain subtypes of childhood acute lymphoblastic leukemia with adverse prognosis, and can be utilized as a diagnostic and prognostic marker in these diseases (Armstrong et al. (2002) *Nat Genet.* 30:41-47).

II. Agents that Modulate Immune Cell Activation

The agents of this invention can modulate, e.g., up or down regulate, expression and/or activity of gene products or fragments thereof encoded by the Gal1 gene or fragment thereof and, thereby, modulate, e.g., up or downregulate, an immune response. For example, overexpression of Gal1 by cHL RS cells decreases the viability of activated T cells and skews the balance towards a Th2 immune response (e.g., by increasing the secretion of Th2 cytokines including IL-4, IL-5, IL-10 and IL-13) and fosters the expansion and/or retention of CD4$^+$ CD25$^{high}$ FOXP3$^+$ $T_{reg}$ cells. The interaction between a Gal1 polypeptide or a fragment thereof and its natural binding partner(s) or a fragment(s) thereof in the context of cHL results in an immunosuppressive Th2/$T_{reg}$-skewed microenvironment. Thus, in one embodiment, agents which block the interactions between a Gal1 polypeptide or a fragment thereof and its natural binding partner(s) or a fragment(s) thereof can enhance an immune response (e.g., restore immune surveillance in cHL). In another embodiment, agents that increase the interactions between a Gal1 polypeptide or a fragment thereof and its natural binding partner(s) or a fragment(s) thereof can decrease an immune response (e.g., immunosuppression). Exemplary agents for modulating a Gal1-mediated immune response include antibodies against Gal1 which inhibit the interactions between a Gal1 polypeptide or a fragment thereof and its natural binding partner(s) or a fragment(s) thereof, small molecules, peptides, peptidomimetics, natural ligands, and derivatives of natural ligands, which inhibit the interactions between a Gal1 polypeptide or a fragment thereof and its natural binding partner(s) or a fragment(s) thereof, and RNA interference, antisense, and nucleic acid aptamers that reduce Gal1 nucleic acids or Gal1 expression products or fragments thereof.

An isolated Gal1 polypeptide or a fragment thereof (or a nucleic acid encoding such a polypeptide), can be used as an immunogen to generate antibodies that bind to said immunogen, using standard techniques for polyclonal and monoclonal antibody preparation. A full-length Gal1 polypeptide can be used, or alternatively, the invention relates to antigenic peptide fragments of Gal1 polypeptide for use as immunogens. An antigenic peptide of Gal1 comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. Preferred epitopes encompassed by the antigenic peptides are regions of Gal1 that mediate ligand specific carbohydrate binding, e.g., the Gal1 carbohydrate recognition domain, amino acids 30 to 90 of human Gal1, and amino acids 62 to 86 of human Gal1. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an antibody binds substantially specifically to a Gal1 polypeptide, or a fragment thereof. In a preferred embodiment, an antibody binds to a Gal1 polypeptide, or a fragment thereof, and blocks the interaction between a Gal1 polypeptide or a fragment thereof and its natural binding partner(s) or a fragment(s) thereof.

A Gal1 immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also Brown et al. (1981) *J. Immunol.* 127:539-46; Brown et al (1980) *J. Biol. Chem.* 255:4980-83; Yeh et al (1976) *Proc. Natl. Acad. Sci.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating an anti-Gal1 monoclonal antibody (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag-4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides antibody can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al International Publication No. WO 91/17271; Winter et al International Publication WO 92/20791; Markland et al. International Publication No. WO 92/15679; Breitling et al. International Publication WO 93/01288; McCafferty et al International Publication No. WO 92/01047; Garrard et al. International Publication No. WO 92/09690; Ladner et al International Publication No. WO 90/02809; Fuchs et al. (1991) *Biotechnology (NY)* 9:1369-1372; Hay et al (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al (1991) *Nature* 352:624-628; Gram et al (1992) *Proc. Natl. Acad. Sci. USA* 89:3576-3580; Garrard et al. (1991) *Biotechnology (NY)* 9:1373-1377; Hoogenboom et al. (1991) *Nucleic Acids Res.* 19:4133-4137; Barbas et al (1991) *Proc. Natl. Acad. Sci. USA* 88:7978-7982; and McCafferty et al (1990) *Nature* 348:552-554.

Additionally, recombinant anti-Gal1 polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171, 496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. No. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology (NY)* 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al).

Additionally, fully human antibodies could be made against a Gal1 immunogen. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified Gal1 immunogen. Spleen cells are harvested and fused to myeloma cells to produce hybridomas. Hybridomas are selected based on their ability to produce antibodies which bind to the Gal1 immunogen. Fully human antibodies would reduce the immunogenicity of such antibodies in a human.

In one embodiment, an antibody for use in the instant invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA*, 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a Gal1 polypeptide or a fragment thereof. In one embodiment, the bispecific antibody could specifically bind to both a Gal1 polypeptide or a fragment thereof and its natural binding partner(s) or a fragment(s) thereof.

Yet another aspect of the invention pertains to anti-Gal1 antibodies that are obtainable by a process comprising, immunizing an animal with an immunogenic Gal1 polypeptide or an immunogenic portion thereof unique to Gal1; and then isolating from the animal antibodies that specifically bind to the polypeptide or a fragment thereof.

In another aspect of this invention, peptides or peptide mimetics can be used to antagonize or promote the interactions between a Gal1 polypeptide or a fragment thereof and its natural binding partner(s) or a fragment(s) thereof. In one embodiment, variants of Gal1 which function as a modulating agent for the respective full length protein, can be identified by screening combinatorial libraries of mutants, e.g., truncation mutants, for antagonist activity. In one embodiment, a variegated library of Gal1 variants is generated by combinatorial mutagenesis at the nucleic acid level and is encoded by a variegated gene library. A variegated library of Gal1 variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of Gal1 (Arkin and Youvan (1992) *Proc. Natl. Acad. Sci. USA* 89:7811-7815; Delagrave et al. (1993) *Protein Eng.* 6(3):327-331). In one embodiment, cell based assays can be exploited to analyze a variegated polypeptide library. For example, a library of expression vectors can be transfected into a cell line which ordinarily synthesizes Gal1. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

In one embodiment, the peptide has an amino acid sequence identical or similar to the Gal1 binding site of its natural binding partner(s) or a fragment(s) thereof. In one embodiment, the peptide competes with a Gal1 polypeptide or a fragment thereof for binding its natural binding partner(s) or a fragment(s) thereof. In a preferred embodiment, the peptide carries carbohydrate moieties recognized by a Gal1 polypeptide or a fragment thereof and said peptide competes with the Gal1 polypeptide or a fragment thereof for binding the Gal1 natural binding partner(s) or a fragment(s) thereof.

Peptides can be produced, typically by direct chemical synthesis, and used e.g., as antagonists of the interactions between a Gal1 polypeptide or a fragment thereof and its natural binding partner(s) or a fragment(s) thereof. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere, J. (1986) *Adv. Drug Res.* 15:29; Veber and Freidinger (1985) *TINS p.* 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as a human Gal1 polypeptide or a fragment thereof, but have one or more peptide linkages optionally replaced by a linkage selected from the group consisting of: —CH2NH—, —CH2S—, —CH2-CH2-, —CH=CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci. pp.* 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982) (—CH(OH)CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred nonpeptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., the interactions between a Gal1 polypeptide or a fragment thereof and its natural binding partner(s) or a fragment(s) thereof. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12: 145).

Examples of methods for the synthesis of molecular libraries can be found in the art, for example in: DeWitt et al. (1993)

*Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gal1 op et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds. In one embodiment, the small molecule binds to the binding site involved in interactions between a Gal1 polypeptide or a fragment thereof and its natural binding partner(s) or a fragment(s) thereof.

The invention also relates to Gal1 chimeric or fusion proteins. As used herein, a Gal1 "chimeric protein" or "fusion protein" comprises a Gal1 molecule or a fragment thereof operatively linked to a non-Gal1 molecule. A "Gal1 molecule" refers to a polypeptide having an amino acid sequence corresponding to Gal1 or a fragment thereof, whereas a "a non-Gal1 molecule" refers to a polypeptide having an amino acid sequence corresponding to a protein which is not substantially homologous to the respective Gal1 molecule, e.g., a protein which is different from the Gal1 molecule, and which is derived from the same or a different organism. Within a Gal1 fusion protein, the Gal1 portion can correspond to all or a portion of a full length Gal1 molecule. In a preferred embodiment, the fusion protein comprises at least one biologically active portion of a Gal1 molecule, e.g., the carbohydrate recognition domain (CRD). Within the fusion protein, the term "operatively linked" is intended to indicate that the Gal1 sequences and the non-Gal1 polypeptide sequences are fused in-frame to each other in such a way as to preserve functions exhibited when expressed independently of the fusion. The non-Gal1 sequences can be fused to the N-terminus or C-terminus of the Gal1 sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. Preferably, the first peptide consists of a portion of Gal1 that comprises at least one biologically active portion of a Gal1 molecule, e.g., the carbohydrate recognition domain (CRD). In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or staggerended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). A polypeptide encoding nucleic acid can be cloned into such an expression vector such that the fusion moiety is linked in-frame to the Gal1 encoding sequences.

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between a Gal1 polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., Gal1 mRNA or a fragment thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, the Gal1 gene or gene products or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, small nucleic acids and/or antisense constructs are oligonucleotide probes that are generated ex vivo and which, when introduced into the cell, results in hybridization with cellular nucleic acids (e.g., Gal1 mRNA or a fragment thereof). Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., Gal1 mRNA or a fragment thereof). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. (1994) Nature 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and nonspecific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) *BioTechniques* 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215:327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc.

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. In vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™. An exemplary Gal1 shRNA target sequence is GCTGCCAGATGGATACGAA (SEQ ID NO: 1).

Ribozyme molecules designed to catalytically cleave cellular mRNA transcripts can also be used to prevent translation of cellular mRNAs (e.g., Gal1 mRNA or a fragment thereof) and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.) and should be delivered to cells which express Gal1 genes or a fragment thereof in vivo. A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes (e.g., the Gal1 gene or a fragment thereof) are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids, antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that regulatable proteins, inhibitory mutants, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g. antibodies, small molecules, peptides, fusion proteins, or small nucleic acids) can be incorporated into pharmaceutical compositions and administered to a subject in vivo. The compositions may contain a single such molecule or agent or any combination of modulatory agents described herein.

III. Methods of Selecting Agents that Modulate Immune Cell Activation

Another aspect of the invention relates to methods of selecting agents (e.g., antibodies, fusion proteins, peptides, small molecules, or small nucleic acids) which modulate an immune response by modulating the interactions between a Gal1 polypeptide or a fragment thereof and its natural binding partner(s) or a fragment(s) thereof. Such methods utilize screening assays, including cell based and non-cell based assays.

In one embodiment, the invention relates to assays for screening candidate or test compounds which bind to, or modulate the activity of, a Gal1 polypeptide or a fragment thereof, e.g., modulate the ability of a Gal1 polypeptide or a fragment thereof to interact with, e.g. bind to, its natural binding partner(s) or a fragment(s) thereof. In one embodiment, a method for identifying an agent to modulate an immune response entails determining the ability of the agent to modulate, e.g. enhance or inhibit, the interactions between a Gal1 polypeptide or a fragment thereof and its natural binding partner(s) or a fragment(s) thereof. Such agents include, without limitation, antibodies, proteins, fusion proteins and small molecules.

In one embodiment, a method for identifying an agent which enhances an immune response entails determining the ability of the candidate agent to inhibit the interactions between a Gal1 polypeptide or a fragment thereof and its natural binding partner(s) or a fragment(s) thereof. In another embodiment, a method for identifying an agent to decrease an immune response entails determining the ability of a candidate agent to enhance the interactions between a Gal1 polypeptide or a fragment thereof and its natural binding partner(s) or a fragment(s) thereof.

In one embodiment, an assay is a cell-based assay, comprising contacting a cell expressing a Gal1 polypeptide or a fragment thereof, with a test compound and determining the ability of the test compound to modulate (e.g. stimulate or inhibit) the binding between a Gal1 polypeptide or a fragment thereof and its natural binding partner(s) or a fragment(s) thereof. Determining the ability of a Gal1 polypeptide or a fragment thereof to bind to, or interact with, a binding partner or a fragment thereof, can be accomplished, e.g., by measuring direct binding or by measuring a parameter of immune cell activation.

For example, in a direct binding assay, a Gal1 polypeptide, a Gal1 binding partner(s), or a fragment(s) thereof, can be coupled with a radioisotope or enzymatic label such that binding of the Gal1 polypeptide or a fragment thereof to its natural binding partner(s) or a fragment(s) thereof can be determined by detecting the labeled molecule in a complex. For example, a Gal1 polypeptide, a Gal1 binding partner(s), or a fragment(s) thereof, can be labeled with $^{125}$I, $^{35}$S, $^{14}$C, or $^{3}$H, either directly or indirectly, and the radioisotope detected by direct counting of radioemission or by scintillation counting. Alternatively, a Gal1 polypeptide, a Gal1 binding partner(s), or a fragment(s) thereof, can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interactions between a Gal1 polypeptide or a fragment thereof and its natural binding partner(s) or a fragment(s) thereof, without the labeling of any of the interactants. For example, a microphysiometer can be used to detect the interactions between a Gal1 polypeptide or a fragment thereof and its natural binding partner(s) or a fragment(s) thereof without the labeling of either a Gal1 polypeptide or a fragment thereof and its natural binding partner(s) or a fragment(s) thereof (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the blocking agents (e.g. antibodies, fusion proteins, peptides, or small molecules) to antagonize the interaction between a given set of polypeptides can be accomplished by determining the activity of one or more members of the set of interacting molecules. For example, the activity of Gal1 can be determined by detecting induction of a cellular second messenger (e.g., H-Ras), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by a Gal1 polypeptide or a fragment thereof. Determining the ability of the blocking agent to bind to or interact with said polypeptide can be accomplished by measuring the ability of an agent to modulate immune responses, for example, by detecting changes in type and amount of cytokine secretion, changes in apoptosis or proliferation, changes in gene expression or activity associated with cellular identity, or by interfering with the ability of said polypeptide to bind to antibodies that recognize a portion thereof.

Agents that block or inhibit interactions between a Gal1 polypeptide or a fragment thereof and its natural binding partner(s) or a fragment(s) thereof (e.g., blocking antibodies to a Gal1 polypeptide or a fragment thereof) can be identified by their ability to inhibit immune cell proliferation, and/or effector function, induce apoptosis, or to induce anergy when added to an in vitro assay. For example, cells can be cultured in the presence of an agent that stimulates signal transduction via an activating receptor. A number of recognized readouts of cell activation can be employed to measure, cell proliferation, apoptosis, or effector function (e.g., antibody production, cytokine production, phagocytosis) in the presence of the activating agent. The ability of a test agent to block this activation can be readily determined by measuring the ability of the agent to effect a decrease in proliferation, increase apoptosis, or effector function being measured, using techniques known in the art.

In yet another embodiment, an assay of the present invention is a cell-free assay in which a Gal1 polypeptide or a fragment thereof, e.g. a biologically active fragment thereof, is contacted with a test compound, and the ability of the test compound to bind to the polypeptide, or biologically active portion thereof, is determined. Binding of the test compound to a Gal1 polypeptide or a fragment thereof, can be determined either directly or indirectly as described above. In a preferred embodiment, the assay includes contacting the Gal1 polypeptide or fragment thereof, with a Gal1 natural binding partner(s) or fragment(s) thereof, to form an assay mixture, contacting the assay mixture with a test compound, and determining the ability of the test compound to interact with the polypeptide in the assay mixture, wherein determining the ability of the test compound to interact with the polypeptide comprises determining the ability of the test compound to preferentially bind to the polypeptide or fragment thereof, as compared to the binding partner.

For example, a Gal1 polypeptide or a fragment thereof and its natural binding partner(s) or a fragment(s) thereof can be used to form an assay mixture and the ability of a polypeptide to block this interaction can be tested by determining the ability of a Gal1 polypeptide or a fragment thereof to bind to the Gal1 natural binding partner(s) or a fragment(s) thereof, by one of the methods described above for determining direct binding. Determining the ability of a Gal1 polypeptide or a fragment thereof and its natural binding partner(s) or a fragment(s) thereof can also be accomplished using a technology such as real-time Biomolecular Interaction Analysis (BIA) (Sjolander, S, and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. A Gal1 polypeptide or a fragment thereof can be immobilized on a BIAcore chip and multiple agents, e.g., blocking antibodies, fusion proteins, peptides, or small molecules, can be tested for binding to the immobilized Gal1 polypeptide or fragment thereof. An example of using the BIA technology is described by Fitz et al. (1997) *Oncogene* 15:613.

The cell-free assays of the present invention are amenable to use of both soluble and/or membrane-bound forms of proteins (e.g., Gal1 polypeptides, Gal1 binding partner(s) polypeptides, and fragments thereof). In the case of cell-free assays in which a membrane-bound form protein is used (e.g., a cell surface Gal1 polypeptide or a fragment thereof or Gal1 natural binding partner(s) or a fragment(s) thereof) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either the Gal1 polypeptide, the Gal1 natural binding partner(s) polypeptide, or fragments thereof, to facilitate separation of complexed from uncomplexed forms of one or both of the proteins, as well as to accommodate automation of the assay. Binding of a test compound to a Gal1 polypeptide, a Gal1 natural binding partner(s) polypeptide, or fragments thereof, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/Gal1 or glutathione-S-transferase/Gal1 natural binding partner(s) fusion proteins, can be adsorbed onto glutathione Sepharose® beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of Gal1 binding or activity determined using standard techniques.

In an alternative embodiment, determining the ability of the test compound to modulate the activity of a Gal1 or Gal1 natural binding partner(s) can be accomplished by determining the ability of the test compound to modulate the expression or activity of a gene, e.g., nucleic acid, or gene product, e.g., polypeptide, that functions downstream of Gal1 or a Gal1 natural binding partner(s), e.g., a polypeptide that functions downstream of the Gal1 natural binding partner(s). For example, levels of second messengers can be determined, the activity of the interactor polypeptide on an appropriate target can be determined, or the binding of the interactor to an appropriate target can be determined as previously described.

In another embodiment, modulators of Gal1 expression are identified in a method wherein a cell is contacted with a candidate compound and the expression of Gal1 mRNA or polypeptide or fragments thereof in the cell is determined. The level of expression of Gal1 mRNA or polypeptide or fragments thereof in the presence of the candidate compound is compared to the level of expression of Gal1 mRNA or polypeptide or fragments thereof in the absence of the candidate compound. The candidate compound can then be identified as a modulator of Gal1 expression based on this comparison. For example, when expression of Gal1 mRNA or polypeptide or fragments thereof is greater (statistically significantly greater) in the presence of the candidate compound than in its absence, the candidate compound is identified as a stimulator of Gal1 expression. Alternatively, when expression of Gal1 mRNA or polypeptide or fragments thereof is reduced (statistically significantly less) in the presence of the candidate compound than in its absence, the candidate compound is identified as an inhibitor of Gal1 expression. The expression level of Gal1 mRNA or polypeptide or fragments thereof in the cells can be determined by methods described herein for detecting Gal1 mRNA or polypeptide or fragments thereof.

In yet another aspect of the invention, Gal1 polypeptides or fragments thereof can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Twabuchi et al. (1993) Oncogene 8:1693-1696; and Brent WO94/10300), to identify other polypeptides which bind to or interact with Gal1 or fragments thereof ("Gal1-binding proteins", "Gal1 binding partners", or "Gal1-bp") and are involved in Gal1 activity. Such Gal1-binding proteins are also likely to be involved in the propagation of signals by the Gal1 polypeptides or Gal1 natural binding partner(s) as, for example, downstream elements of a Gal1-mediated signaling pathway. Alternatively, such Gal1-binding polypeptides may be Gal1 inhibitors.

The two-hybrid system is based on the modular nature of most transcription factors, which consist of separable DNA-binding and activation domains. Briefly, the assay utilizes two different DNA constructs. In one construct, the gene that codes for a Gal1 polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming a Gal1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with the Gal1 polypeptide.

In another aspect, the invention pertains to a combination of two or more of the assays described herein. For example, a modulating agent can be identified using a cell-based or a cell-free assay, and the ability of the agent to modulate the activity of a Gal1 polypeptide or a fragment thereof can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

IV. Pharmaceutical Compositions

Gal1 modulating agents (e.g., agents that inhibit or promote the interactions between a Gal1 polypeptide or a fragment thereof and its natural binding partner(s) or a fragment thereof, including, e.g., blocking antibodies, peptides, fusion proteins, or small molecules) can be incorporated into pharmaceutical compositions suitable for administration to a subject. Such compositions typically comprise the antibody, peptide, fusion protein or small molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., blocking antibodies, peptides, fusion proteins, or small molecules that inhibit the interactions between a Gal1 polypeptide or a fragment thereof and its natural binding partner(s) or a fragment(s) thereof) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity of Gal1 nucleic acid, polypeptide, or fragments thereof. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the scope of knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such polypeptides may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985); and Thorpe et al. "The Preparation And Cytotoxic Properties Of Antibody- Toxin Conjugates", Immunol. Rev. 62:119-58 (1982). Alternatively, an antibody can be conjugated to a second antibody to form an antibody heteroconjugate as described by Segal in U.S. Pat. No. 4,676,980.

The above described modulating agents may be administered it the form of expressible nucleic acids which encode said agents. Such nucleic acids and compositions in which they are contained, are also encompassed by the present invention. For instance, the nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The Gal1 molecules, e.g., the Gal1 nucleic acid molecules, polypeptides, polypeptide homologues, antibodies, and fragments thereof, described herein can be used in one or more of the following methods: a) screening assays; b) predictive medicine (e.g., diagnostic assays, prognostic assays, and monitoring clinical trials); and c) methods of treatment (e.g., therapeutic and prophylactic, e.g., by up- or down-modulating the immune response). As described herein, a Gal1 polypeptide or fragment thereof of the invention has one or more of the following activities: 1) binds to and/or modulates the activity of its natural binding partner(s), 2) modulates intra- or intercellular signaling, 3) modulates activation of T lymphocytes, 4) modulates the immune response of an organism, e.g., a mammalian organism, such as a mouse or human. See, for example, Toscano et al. (2007) *Cyt Growth Fact Rev* 18:57-71; Camby et al. (2006) *Glycobiol* 16:137R-157R, each of which is incorporated herein, by reference, in its entirety.

The isolated nucleic acid molecules of the invention can be used, for example, to express a Gal1 polypeptide or a fragment thereof (e.g., via a recombinant expression vector in a host cell in gene therapy applications), to detect Gal1 mRNA or a fragment thereof (e.g., in a biological sample) or a genetic alteration in a Gal1 gene, and to modulate Gal1 activity, as described further below. The Gal1 polypeptides or fragments thereof can be used to treat conditions or disorders characterized by insufficient or excessive production of a Gal1 polypeptide or fragment thereof or production of Gal1 polypeptide inhibitors. In addition, the Gal1 polypeptides or fragments thereof can be used to screen for naturally occurring Gal1 binding partner(s), to screen for drugs or compounds which modulate Gal1 activity, as well as to treat conditions or disorders characterized by insufficient or excessive production of Gal1 polypeptide or a fragment thereof or production of Gal1 polypeptide forms which have decreased, aberrant or unwanted activity compared to Gal1 wild-type polypeptides or fragments thereof (e.g., immune system disorders such as severe combined immunodeficiency, multiple sclerosis, systemic lupus erythematosus, type I diabetes mellitus, lymphoproliferative syndrome, inflammatory bowel disease, allergies, asthma, graft-versus-host disease, and transplant rejection; immune responses to infectious pathogens such as bacteria and viruses; and immune system cancers such as cancers including mature B Cell Neoplasms (e.g. Chronic lymphocytic leukemia/small lymphocytic lymphoma, B-cell prolymphocytic leukemia, Lymphoplasmacytic lymphoma/Waldenstrom macroglobulinemia, Splenic marginal zone lymphoma, Plasma cell neoplasms, Extranodal marginal zone B cell lymphoma (MALT lymphoma), Nodal marginal zone B cell lymphoma, Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, Lymphomatoid granulomatosis), Mature T cell and Natural Killer (NK) Cell Neoplasms (e.g. T cell prolymphocytic leukemia, T cell large granular lymphocytic leukemia, Aggressive NK cell leukemia, Adult T cell leukemia/lymphoma, Nasal type extranodal NK/T cell lymphoma, Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Angioimmunoblastic T cell lymphoma, Unspecified peripheral T cell lymphoma, Anaplastic large cell lymphoma), Hodgkin lymphoma (e.g. Nodular lymphocyte-predominant Hodgkin lymphoma, Classical Hodgkin lymphoma), Immunodeficiency-Associated Lymphoproliferative Disorders (i.e. those associated with a primary immune disorder, those associated with the Human Immunodeficiency Virus (HIV), those associated with Methotrexate therapy, those associated with organ transplantation), Histiocytic and Dendritic Cell Neoplasms (e.g. Histiocytic sarcoma, Langerhans cell histiocytosis, Langerhans cell sarcoma, Interdigitating dendritic cell sarcoma/tumour, Follicular dendritic cell sarcoma/tumour, Unspecified dendritic cell sarcoma), thymomas, hamartomatous tumors arising in a vascular organ (e.g. lung, liver, uterus, hypothalmus, kidney, spleen, skeletal muscle, abdominal wall, adrenal gland, bone marrow, omentum, lymph node, skin), malignant angiosarcomas derived from such hamartomatous tumors, hemangiomas, Cowden syndrome, Lhermitte-Duclos disease, and Bannayan-Zonana syndrome). Moreover, the anti-Gal1 antibodies or fragments thereof of the invention can be used to detect and isolate Gal1 polypeptides or fragments thereof, regulate the bioavailability of Gal1 polypeptides or fragments thereof, and modulate Gal1 activity, e.g., by modulating the interaction between a Gal1 polypeptide or a fragment thereof and its natural binding partner(s) or a fragment(s) thereof.

A. Screening Assays

In one aspect, the invention relates to a method for preventing in a subject, a disease or condition associated with an unwanted or less than desirable immune response. Subjects at risk for a disease that would benefit from treatment with the claimed agents or methods can be identified, for example, by any or a combination of diagnostic or prognostic assays known in the art and described herein (see, for example, agents and assays described in III. Methods of Selecting Agents that Modulate Immune Cell Activation).

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the Gal1 nucleotide sequences, described herein, can be used to map the location of the Gal1 genes on a chromosome. The mapping of the Gal1 sequences to chromosomes is an important first step in correlating these sequences with genes associated with disease.

Briefly, Gal1 genes can be mapped to chromosomes by preparing PCR primers (preferably 15-25 bp in length) from the Gal1 nucleotide sequences. Computer analysis of the Gal1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the Gal1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio, P. et al. (1983) Science 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the Gal1 nucleotide sequences to design oligonucleotide primers, sublocalization can be achieved with panels of fragments from specific chromosomes. Other mapping strategies which can similarly be used to map a Gal1 sequence to its chromosome include in situ hybridization (described in Fan, Y. et al. (1990) Proc. Natl. Acad. Sci. USA 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data (such data are found, for example, in McKusick, V., Mendelian Inheritance in Man, available online through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature 325:783-787.

Moreover, differences in the DNA sequences between individuals affected and unaffected with a disease associated with the Gal1 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The Gal1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the Gal1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The Gal1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of Gal1 can provide positive individual identification with a panel of perhaps 10 to 1,000 primers which each yield a noncoding amplified sequence of 100 bases. If predicted Gal1 coding sequences are used, a more appropriate number of primers for positive individual identification would be 500-2000.

If a panel of reagents from Gal1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Gal1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of Gal1 are particularly appropriate for this use as greater numbers of polymorphisms occur in the noncoding regions, making it easier to differentiate individuals using this technique. Examples of polynucleotide reagents include the Gal1 nucleotide sequences or portions thereof, e.g., fragments derived from the noncoding regions of Gal1 having a length of at least 20 bases, preferably at least 30 bases.

The Gal1 nucleotide sequences described herein can further be used to provide polynucleotide reagents, e.g., labeled or labelable probes which can be used in, for example, an in situ hybridization technique, to identify a specific tissue, e.g., lymphocytes. This can be very useful in cases where a forensic pathologist is presented with a tissue of unknown origin. Panels of such Gal1 probes can be used to identify tissue by species and/or by organ type.

In a similar fashion, these reagents, e.g., Gal1 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining Gal1 polypeptide and/or nucleic acid expression as well as Gal1 activity, in the context of a biological sample (e.g., blood, serum, cells, or tissue) to thereby determine whether an individual is afflicted with a disease or disorder, or is at risk of developing a disorder, associated with aberrant or unwanted Gal1 expression or activity. The invention also provides for prognostic (or predictive) assays for determining whether an individual is at risk of developing a disorder associated with Gal1 polypeptide, nucleic acid expression or activity. For example, mutations in a Gal1 gene can be assayed in a biological sample.

Such assays can be used for prognostic or predictive purpose to thereby prophylactically treat an individual prior to the onset of a disorder characterized by or associated with Gal1 polypeptide, nucleic acid expression or activity.

Another aspect of the invention pertains to monitoring the influence of agents (e.g., drugs, compounds) on the expression or activity of Gal1 in clinical trials.

These and other agents are described in further detail in the following sections.

1. Diagnostic Assays

An exemplary method for detecting the presence or absence of Gal1 polypeptide or nucleic acid or fragments thereof in a biological sample involves obtaining a biological sample from a test subject and contacting the biological sample with a compound or an agent capable of detecting Gal1 polypeptide or nucleic acid that encodes Gal1 polypeptide (e.g., mRNA or genomic DNA) or fragments thereof such that the presence of Gal1 polypeptide or nucleic acid or fragments thereof is detected in the biological sample. A preferred agent for detecting Gal1 mRNA, genomic DNA, or fragments thereof is a labeled nucleic acid probe capable of hybridizing to Gal1 mRNA, genomic DNA, or fragments thereof. The nucleic acid probe can be, for example, full length Gal1 nucleic acid, or a portion thereof, such as an oligonucleotide of at least 15, 30, 50, 100, 250 or 500 nucleotides in length and sufficient to specifically hybridize under stringent conditions to Gal1 mRNA or genomic DNA. Other suitable probes for use in the diagnostic assays of the invention are described herein.

A preferred agent for detecting a Gal1 polypeptide or a fragment thereof is an antibody capable of binding to a Gal1 polypeptide, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect Gal1 mRNA, polypeptide, genomic DNA, or fragments thereof, in a biological sample in vitro as well as in vivo. For example, in vitro techniques for detection of Gal1 mRNA or a fragment thereof include Northern hybridizations and in situ hybridizations. In vitro techniques for detection of Gal1 polypeptide include enzyme linked immunosorbent assays (ELISAs), Western blots, immunoprecipitations and immunofluorescence. In vitro techniques for detection of Gal1 genomic DNA or a fragment thereof include Southern hybridizations. Furthermore, in vivo techniques for detection of a Gal1 polypeptide or a fragment thereof include introducing into a subject a labeled anti-Gal1 antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Gal1 polypeptide, mRNA, genomic DNA, or fragments thereof, such that the presence of Gal1 polypeptide, mRNA, genomic DNA, or fragments thereof, is detected in the biological sample, and comparing the presence of Gal1 polypeptide, mRNA, genomic DNA, or fragments thereof, in the control sample with the presence of Gal1 polypeptide, mRNA, genomic DNA, or fragments thereof in the test sample.

The invention also encompasses kits for detecting the presence of a Gal1 nucleic acid, polypeptide, or fragments thereof, in a biological sample. For example, the kit can comprise a labeled compound or agent capable of detecting a Gal1 nucleic acid, polypeptide, or fragments thereof in a biological sample; means for determining the amount of the Gal1 nucleic acid, polypeptide, or fragments thereof in the sample; and means for comparing the amount of the Gal1 nucleic acid, polypeptide, or fragments thereof in the sample with a standard. The compound or agent can be packaged in a suitable container. The kit can further comprise instructions for using the kit to detect the Gal1 nucleic acid, polypeptide, or fragments thereof.

2. Prognostic Assays

The diagnostic methods described herein can furthermore be utilized to identify subjects having or at risk of developing a disease or disorder associated with aberrant or unwanted Gal1 expression or activity. As used herein, the term "aberrant" includes a Gal1 expression or activity which deviates from the wild type Gal1 expression or activity. Aberrant expression or activity includes increased or decreased expression or activity, as well as expression or activity which does not follow the wild type developmental pattern of expression or the subcellular pattern of expression. For example, aberrant Gal1 expression or activity is intended to include the cases in which a mutation in the Gal1 gene or regulatory sequence thereof causes the Gal1 gene to be under-expressed or over-expressed and situations in which such mutations result in a non-functional Gal1 polypeptide or a polypeptide which does not function in a wild-type fashion, e.g., a polypeptide which does not interact with a Gal1 binding partner(s) or one which interacts with a non-Gal1 binding partner(s). As used herein, the term "unwanted" includes an unwanted phenomenon involved in a biological response such as immune cell activation. For example, the term unwanted includes a Gal1 expression or activity which is undesirable in a subject.

The assays described herein, such as the preceding diagnostic assays or the following assays, can be utilized to identify a subject having or at risk of developing a disorder associated with a misregulation in Gal1 polypeptide activity or nucleic acid expression, such as an autoimmune disorder, an immunodeficiency disorder, an immune system cancer, e.g., Hodgkin lymphoma, or a tendency to have spontaneous abortions. Alternatively, the prognostic assays can be utilized to identify a subject having or at risk for developing a disorder associated with a misregulation of Gal1 polypeptide activity or nucleic acid expression, such as an autoimmune disorder, and immunodeficiency disorder, or an immune system cancer, e.g., Hodgkin lymphoma. Thus, the present invention provides a method for identifying a disease or disorder associated with aberrant or unwanted Gal1 expression or activity in which a test sample is obtained from a subject and Gal1 polypeptide or nucleic acid (e.g., mRNA or genomic DNA) is detected, wherein the presence of Gal1 polypeptide or nucleic acid is diagnostic for a subject having or at risk of developing a disease or disorder associated with aberrant or unwanted Gal1 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant or unwanted Gal1 expression or activity. For example, such methods can be used to determine whether a subject can be effectively treated with an agent for an autoimmune disorder, immunodeficiency disorder, or immune system cancer, e.g., Hodgkin lymphoma. Thus, the present invention provides methods for determining whether a subject can be effectively treated with an agent for a disorder associated with aberrant or unwanted Gal1 expression or activity in which a test sample is obtained and Gal1 polypeptide or nucleic acid expression or activity is detected (e.g., wherein the abundance of Gal1 polypeptide or nucleic acid expression or activity is diagnostic for a subject that can be administered the agent to treat a disorder associated with aberrant or unwanted Gal1 expression or activity).

The methods of the invention can also be used to detect genetic alterations in a Gal1 gene, thereby determining if a subject with the altered gene is at risk for a disorder characterized by misregulation in Gal1 polypeptide activity or nucleic acid expression, such as an autoimmune disorder, an immunodeficiency disorder, or an immune system cancer, e.g., Hodgkin lymphoma. In preferred embodiments, the methods include detecting, in a sample of cells from the subject, the presence or absence of a genetic alteration characterized by at least one alteration affecting the integrity of a gene encoding a Gal1 polypeptide, or the mis-expression of the Gal1 gene. For example, such genetic alterations can be detected by ascertaining the existence of at least one of 1) a deletion of one or more nucleotides from a Gal1 gene, 2) an addition of one or more nucleotides to a Gal1 gene, 3) a substitution of one or more nucleotides of a Gal1 gene, 4) a chromosomal rearrangement of a Gal1 gene, 5) an alteration in the level of a messenger RNA transcript of a Gal1 gene, 6) aberrant modification of a Gal1 gene, such as of the methylation pattern of the genomic DNA, 7) the presence of a non-wild type splicing pattern of a messenger RNA transcript of a Gal1 gene, 8) a non-wild type level of a Gal1 polypeptide, 9) allelic loss of a Gal1 gene, and 10) inappropriate post-translational modification of a Gal1 polypeptide. As described herein, there are a large number of assays known in the art which can be used for detecting alterations in a Gal1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683, 202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a Gal1 gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a Gal1 gene under conditions such that hybridization and amplification of the Gal1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Gal1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Gal1 can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in Gal1 can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Gal1 gene and detect mutations by comparing the sequence of the sample Gal1 with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad. Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the Gal1 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type Gal1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217: 286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Gal1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a Gal1 sequence, e.g., a wild-type Gal1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Gal1 genes. For example, single strand conformation polymorphism (SSCP) may be used to detect differences in electrophoretic mobility between mutant and wild type nucleic acids (Orita et al. (1989) Proc Natl. Acad. Sci. USA 86:2766; see also Cotton (1993) Mutat. Res. 285:125-144 and Hayashi (1992) Genet. Anal. Tech. Appl. 9:73-79). Single-stranded DNA fragments of sample and control Gal1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313: 495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell. Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Gal1 gene.

Furthermore, any cell type or tissue in which Gal1 is expressed may be utilized in the prognostic assays described herein.

3. Monitoring of Effects During Clinical Trials

Monitoring the influence of agents (e.g., drugs) on the expression or activity of a Gal1 polypeptide or a fragment thereof (e.g., the modulation of cell proliferation and/or migration) can be applied not only in basic drug screening, but also in clinical trials. For example, the effectiveness of an agent determined by a screening assay as described herein to increase Gal1 gene expression, polypeptide levels, or upregulate Gal1 activity, can be monitored in clinical trials of subjects exhibiting decreased Gal1 gene expression, polypeptide levels, or downregulated Gal1 activity. Alternatively, the effectiveness of an agent determined by a screening assay to decrease Gal1 gene expression, polypeptide levels, or downregulate Gal1 activity, can be monitored in clinical trials of subjects exhibiting increased Gal1 gene expression, polypeptide levels, or Gal1 activity. In such clinical trials, the expression or activity of a Gal1 gene, and preferably, other genes that have been implicated in, for example, a Gal1-associated disorder can be used as a "read out" or marker of the phenotype of a particular cell.

For example, and not by way of limitation, genes, including Gal1, that are modulated in cells by treatment with an agent (e.g., compound, drug or small molecule) which modulates Gal1 activity (e.g., identified in a screening assay as described herein) can be identified. Thus, to study the effect of agents on Gal1-associated disorders (e.g., disorders characterized by dysregulated Gal1 activity), for example, in a clinical trial, cells can be isolated and RNA prepared and analyzed for the levels of expression of Gal1 and other genes implicated in the Gal1-associated disorder, respectively. The levels of gene expression (e.g., a gene expression pattern) can be quantified by Northern blot analysis or RT-PCR, as described herein, or alternatively by measuring the amount of polypeptide produced, by one of the methods as described herein, or by measuring the levels of activity of Gal1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression of a Gal1 polypeptide, mRNA, genomic DNA, or fragments thereof in the preadministration sample; (iii) obtaining one or more post-administration samples from the subject; (iv) detecting the level of expression or activity of the Gal1 polypeptide, mRNA, genomic DNA, or fragments thereof in the post-administration samples; (v) comparing the level of expression or activity of the Gal1 polypeptide, mRNA, genomic DNA, or fragments thereof in the pre-administration sample with the Gal1 polypeptide, mRNA, or genomic DNA in the post administration sample or samples; and (vi) altering the administration of the agent to the subject accordingly. For example, increased administration of the agent may be desirable to increase the expression or activity of Gal1 to higher levels than detected, i.e., to increase the effectiveness of the agent. Alternatively, decreased administration of the agent may be desirable to decrease expression or activity of Gal1 to lower levels than detected, i.e., to decrease the effectiveness of the agent. According to such an embodiment, Gal1 expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a disorder characterized by insufficient or excessive production of Gal1 polypeptides or production of Gal1 protein forms which have decreased or aberrant activity compared to Gal1 wild type protein. Moreover, the anti-Gal1 antibodies of the invention can be used to detect and isolate Gal1 polypeptides or fragments thereof, regulate the bioavailability of Gal1 polypeptides or fragments thereof, and modulate Gal1 activity e.g., by modulating the interaction of a Gal1 polypeptide or a fragment thereof with its natural binding partner(s) or fragments(s) thereof.

1. Prophylactic Methods

In one aspect, the invention provides a method for preventing in a subject, a disease or condition associated with an aberrant or unwanted Gal1 expression or activity, by administering to the subject a Gal1 polypeptide or a fragment thereof or an agent which modulates Gal1 expression or at least one Gal1 activity. Subjects at risk for a disease or disorder which is caused or contributed to by aberrant or unwanted Gal1 expression or activity can be identified by, for example, any or a combination of diagnostic or prognostic assays as described herein. Administration of a prophylactic agent can occur prior to the manifestation of symptoms characteristic of the Gal1 aberrancy, such that a disease or disorder is prevented or, alternatively, delayed in its progression. Depending on the type of Gal1 aberrancy, for example, a Gal1 polypeptide, Gal1 agonist or Gal1 antagonist (e.g., an anti-Gal1 antibody or a combination of anti-Gal1 and antibodies against other immune related targets) agent can be used for treating the subject. The appropriate agent can be determined based on screening assays described herein.

2. Therapeutic Methods

Another aspect of the invention pertains to methods of modulating Gal1 expression or activity or interaction with its natural binding partner(s), for therapeutic purposes. Gal1 has been demonstrated to inhibit the viability of $CD3^+$ cells and $CD4^+$ T cells and contribute to a Th1/Th2 imbalance. Accordingly, the activity and/or expression of Gal1, as well as the interaction between a Gal1 polypeptide or a fragment thereof and its natural binding partner(s) or a fragment(s) thereof can be modulated in order to modulate the immune response.

Modulatory methods of the invention involve contacting a cell with a Gal1 polypeptide or a fragment thereof or agent that modulates one or more of the activities of Gal1 polypeptide activity associated with the cell, e.g., an agent that modulates expression or activity of Gal1 and/or modulates the interaction of a Gal1 polypeptide or a fragment thereof and its natural binding partner(s) or a fragment(s) thereof. An agent that modulates Gal1 polypeptide activity can be an agent as described herein, such as a nucleic acid or a polypeptide, a naturally-occurring binding partner of a Gal1 polypeptide, a Gal1 antibody, a combination of Gal1 antibodies and antibodies against other immune related targets, a Gal1 agonist or antagonist, a peptidomimetic of a Gal1 agonist or antagonist, a Gal1 peptidomimetic, other small molecule, or small RNA directed against a Gal1 nucleic acid gene expression product.

An agent that modulates the expression of Gal1 is, e.g., an antisense nucleic acid molecule, RNAi molecule, shRNA or other small RNA molecule, triplex oligonucleotide, ribozyme, or recombinant vector for expression of a Gal1 polypeptide. For example, an oligonucleotide complementary to the area around a Gal1 polypeptide translation initiation site can be synthesized. One or more antisense oligonucleotides can be added to cell media, typically at 200 µg/ml, or administered to a patient to prevent the synthesis of a Gal1 polypeptide. The antisense oligonucleotide is taken up by cells and hybridizes to a Gal1 mRNA to prevent translation. Alternatively, an oligonucleotide which binds double-stranded DNA to form a triplex construct to prevent DNA unwinding and transcription can be used. As a result of either, synthesis of Gal1 polypeptide is blocked. When Gal1 expression is modulated, preferably, such modulation occurs by a means other than by knocking out the Gal1 gene.

Agents which modulate expression, by virtue of the fact that they control the amount of Gal1 in a cell, also modulate the total amount of Gal1 activity in a cell.

In one embodiment, the agent the modulates Gal1 stimulates one or more Gal1 activities. Examples of such stimulatory agents include active Gal1 polypeptide or a fragment thereof and a nucleic acid molecule encoding Gal1 or a fragment thereof that has been introduced into the cell. In another embodiment, the agent inhibits one or more Gal1 activities. In a preferred embodiment, the agent inhibits or enhances the interaction of Gal1 with its natural binding partner(s). Examples of such inhibitory agents include antisense Gal1 nucleic acid molecules, anti-Gal1 antibodies, Gal1 inhibitors, and compounds identified in the subject screening assays.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or downmodulation of a Gal1 polypeptide or a fragment thereof, e.g., a disorder characterized by unwanted, insufficient, or aberrant expression or activity of a Gal1 polypeptide or nucleic acid molecule or fragments thereof. In one embodiment, the method involves administering an agent (e.g., an agent identified by a screening assay described herein), or combination of agents that modulates (e.g., upregulates or downregulates) Gal1 expression or activity. In another embodiment, the method involves administering a Gal1 polypeptide or nucleic acid molecule as therapy to compensate for reduced, aberrant, or unwanted Gal1 expression or activity.

Stimulation of Gal1 activity is desirable in situations in which Gal1 is abnormally downregulated and/or in which increased Gal1 activity is likely to have a beneficial effect. Likewise, inhibition of Gal1 activity is desirable in situations in which Gal1 is abnormally upregulated and/or in which decreased Gal1 activity is likely to have a beneficial effect.

Exemplary agents for use in downmodulating Gal1 (i.e., Gal1 antagonists) include, e.g., antisense nucleic acid molecules, antibodies that recognize and block Gal1, combinations of antibodies that recognize and block Gal1 and antibodies that recognize and block other immune related targets, and compounds that block the interaction of a Gal1 polypeptide or a fragment thereof with its naturally occurring binding partner(s) or fragment(s) thereof on an immune cell. Exemplary agents for use in upmodulating Gal1 (i.e., Gal1 agonists) include, e.g., nucleic acid molecules encoding Gal1 polypeptides, multivalent forms of Gal1, compounds that increase the expression of Gal1, compounds that enhance the interaction of Gal1 with its naturally occurring binding partner(s) and cells that express Gal1.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy, either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regiment and dosages of these aforementioned chemotherapeutic drugs that are therapeutically effective will depend on the particular immune disorder, e.g., Hodgkin lymphoma, being treated, the extent of the disease and other factors familiar to the physician of skill in the art and can be determined by the physician.

3. Downregulation of Immune Responses

There are numerous embodiments of the invention for modulating the interactions between a Gal1 polypeptide or a fragment thereof and its natural binding partner(s) or a fragment(s) thereof to thereby downregulate downregulate immune responses. Downregulation can be in the form of inhibiting or blocking an immune response already in progress, or may involve preventing the induction of an immune response. The functions of activated immune cells can be inhibited by down-regulating immune cell responses, or by inducing specific anergy in immune cells, or both.

For example, the immune response can be downmodulated and/or anergy can be induced using, for example, Gal1 polypeptides (e.g., soluble forms of Gal1 or Gal1 fusion polypeptides) and agents that promote binding of a Gal1 polypeptide or a fragment thereof and its natural binding partner(s) or a fragment(s) thereof (e.g., Gal1 peptide mimetics), identified by the methods described herein.

In one embodiment, fusion proteins comprising a first Gal1 peptide fused to a second peptide can be used to enhance the interaction of a Gal1 polypeptide or a fragment thereof and its natural binding partner(s) or a fragment(s) thereof on an immune cell, to thereby downmodulate immune responses. In one embodiment, the second peptide blocks an activity of another immune related antigen to further downmodulate immune responses. Alternatively, two separate agents that downmodulate immune responses can be combined as a single composition or administered separately (simultaneously or sequentially) to more effectively downregulate immune cell mediated immune responses in a subject. For instance, a Gal1 polypeptide can be combined with a B7 polypeptide, or with a combination of blocking antibodies (e.g., antibodies against Gal1 polypeptide with anti-B7-1 and/or anti-B7-2 monoclonal antibodies). Furthermore, a therapeutically active amount of one or more of the subject agents, can be used in conjunction with other downmodulating reagents to influence immune responses. Examples of other immunomodulating reagents include, without limitation, antibodies that block a costimulatory signal, (e.g., against CD28 or ICOS), antibodies that act as agonists of CTLA4, and/or antibodies against other immune cell markers (e.g., against CD40, against CD40 ligand, or against cytokines), fusion proteins (e.g., CTLA4-Fc), immunosuppressive drugs, (e.g., rapamycin, cyclosporine A, FK506, etc.), or chemotherapy drugs (e.g., adriamycin, bleomycin, vinblastine, dacarbazine, mechloretamine, vincristine, prednisone, procarbazine, etc.).

The Gal1 polypeptides may also be useful in the construction of therapeutic agents which block immune cell function by destruction of cells. For example, portions of a Gal1 polypeptide can be linked to a toxin to make a cytotoxic agent capable of triggering the destruction of cells to which it binds.

For making cytotoxic agents, polypeptides of the invention may be linked, or operatively attached, to toxins using techniques that are known in the art, e.g., via crosslinking or recombinant DNA techniques. The preparation of immunotoxins is, in general, well known in the art (see, e.g., U.S. Pat. No. 4,340,535 and EP 44167, both incorporated herein by reference). Numerous types of disulfide bond-containing linkers are known which can successfully be employed to conjugate the toxin moiety with a polypeptide. In one embodiment, linkers that contain a disulfide bond that is sterically "hindered" are to be preferred, due to their greater stability in vivo, thus preventing release of the toxin moiety prior to binding at the site of action.

A wide variety of toxins are known that may be conjugated to polypeptides or antibodies of the invention. Examples include: numerous useful plant-, fungus- or even bacteria-derived toxins, which, by way of example, include: various A chain toxins, particularly ricin A chain; ribosome inactivating proteins such as saporin or gelonin; alpha-sarcin; aspergillin; restrictocin; and ribonucleases such as placental ribonuclease, angiogenic, diphtheria toxin, or pseudomonas exotoxin. A preferred toxin moiety for use in connection with the invention is toxin A chain which has been treated to modify or remove carbohydrate residues, deglycosylated A chain. (U.S. Pat. No. 5,776,427).

Upregulating or enhancing interactions between a Gal1 polypeptide or a fragment thereof and its natural binding partner(s) or a fragment(s) thereof is useful to downmodulate the immune response, e.g., in situations of tissue, skin and organ transplantation, in graft-versus-host disease (GVHD), or in autoimmune diseases such as systemic lupus erythematosus, and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of a polypeptide which enhances interactions between Gal1 polypeptide or a fragment thereof and its natural binding partner(s) or a fragment(s) thereof, alone or in conjunction with another downmodulatory agent, prior to or at the time of transplantation can promote the generation of an downregulated immune response. Moreover, enhancement of interactions between a Gal1 polypeptide or a fragment thereof and its natural binding partner(s) or a fragment(s) thereof may also be sufficient to anergize the immune cells, thereby inducing tolerance in a subject. Induction of long-term tolerance by enhancing interactions between a Gal1 polypeptide or a fragment thereof and its natural binding partner(s) or a fragment(s) thereof may avoid the necessity of repeated administration of these blocking reagents.

To achieve sufficient immunosuppression or tolerance in a subject, it may also be desirable to block the costimulatory function of other polypeptides. For example, it may be desirable to block the function of B7-1, B7-2, or B7-1 and B7-2 by administering a soluble form of a combination of peptides having an activity of each of these antigens, blocking antibodies against these antigens or blocking small molecules (separately or together in a single composition) prior to or at the time of transplantation. Alternatively, it may be desirable to promote inhibitory activity of a PD-1 ligand or PD-1 and inhibit a costimulatory activity of B7-1 and/or B7-2. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune cell markers or soluble forms of other receptor ligand pairs (e.g., agents that disrupt the interaction between CD40 and CD40 ligand (e.g., anti CD40 ligand antibodies)), antibodies against cytokines, or immunosuppressive drugs.

Downmodulation of immune responses are also useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms.

Administration of reagents which enhance interactions between a Gal1 polypeptide or a fragment thereof and its natural binding partner(s) or a fragment(s) thereof are useful for inhibiting immune cell activation and preventing production of autoantibodies or cytokines which may be involved in the disease process. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see, e.g., Paul ed., *Fundamental Immunology*, Raven Press, New York, Third Edition 1993, chapter 30).

Inhibition of immune cell activation is useful therapeutically in the treatment of allergy and allergic reactions, e.g., by inhibiting IgE production. An agent that promotes interactions between a Gal1 polypeptide or a fragment thereof and its natural binding partner(s) or a fragment(s) thereof can be administered to an allergic subject to inhibit immune cell mediated allergic responses in the subject. Allergic reactions can be systemic or local in nature, depending on the route of entry of the allergen and the pattern of deposition of IgE on mast cells or basophils. Thus, inhibition of immune cell mediated allergic responses locally or systemically by tailored administration of an agent that promotes interactions between a Gal1 polypeptide or a fragment thereof and its natural binding partner(s) or a fragment(s) thereof.

Inhibition of immune cell activation through enhancement of interactions between a Gal1 polypeptide or a fragment thereof and its natural binding partner(s) or a fragment(s) thereof may also be important therapeutically in viral infections of immune cells. For example, in the acquired immune deficiency syndrome (AIDS), viral replication is stimulated by immune cell activation. Modulation of these interactions may result in inhibition of viral replication and thereby ameliorate the course of AIDS.

In an additional embodiment, in performing any of the methods described herein, it is within the scope of the invention to downregulate an immune response by administering one or more additional agents. For example, the use of other agents known to downregulate the immune response can be used in conjunction with an agent that stimulates Gal1 activity or interactions between a Gal1 polypeptide or a fragment thereof and its natural binding partner(s) or a fragment(s) thereof.

4. Upregulation of Immune Responses

Also useful therapeutically is the inhibition of interactions between a Gal1 polypeptide or a fragment thereof and its natural binding partner(s) or a fragment(s) thereof to thereby upregulate immune responses. Upregulation of immune responses can be in the form of enhancing an existing immune response or eliciting an initial immune response. For instance, enhancing an immune response using the subject compositions and methods is useful in cases of infections with microbes (e.g., bacteria, viruses, or parasites). In one embodiment, an agent that blocks interactions between a Gal1 polypeptide or a fragment thereof and its natural binding partner(s) or a fragment(s) thereof is used to enhance the immune response. Such an agent (e.g., a Gal1 blocking antibody) is therapeutically useful in situations where upregulation of antibody and cell-mediated responses would be beneficial. Exemplary disorders include cancer, especially Hodgkin lymphoma, viral skin diseases, such as Herpes or shingles, in which case such an agent can be delivered topically to the skin. In addition, systemic viral diseases such as influenza, the common cold, and encephalitis might be alleviated by systemic administration of such agents.

Alternatively, immune responses can be enhanced in an infected patient through an ex vivo approach, for instance, by removing immune cells from the patient, contacting immune cells in vitro with an agent that blocks interactions between a Gal1 polypeptide or a fragment thereof and its natural binding partner(s) or a fragment(s) thereof, and reintroducing the in vitro stimulated immune cells into the patient.

In certain instances, it may be desirable to further administer other agents that upregulate immune responses, for example, forms of B7 family members that transduce signals via costimulatory receptors, in order to further augment the immune response.

An agent that inhibits Gal1 activity or interactions between a Gal1 polypeptide or a fragment thereof and its natural binding partner(s) or a fragment(s) thereof, can be used prophylactically in vaccines against various polypeptides, e.g., polypeptides derived from pathogens. Immunity against a pathogen, e.g., a virus, can be induced by vaccinating with a viral polypeptide along with an agent that inhibits Gal1 activity or interactions between a Gal1 polypeptide or a fragment thereof and its natural binding partner(s) or a fragment(s) thereof, in an appropriate adjuvant. Alternately, a vector comprising genes which encode for both a pathogenic antigen and a form of Gal1 that blocks interactions between a Gal1 polypeptide or a fragment thereof and its natural binding partner(s) or a fragment(s) thereof can be used for vaccination. Nucleic acid vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. (1996) J. Biotechnol. 44:37)). Alternatively, nucleic acid vaccines can be administered by non-invasive means. For example, pure or lipid-formulated DNA can be delivered to the respiratory system or targeted elsewhere, e.g., Peyers patches by oral delivery of DNA (Schubbert (1997) Proc. Natl. Acad. Sci. USA 94:961). Attenuated microorganisms can be used for delivery to mucosal surfaces (Sizemore et al. (1995) Science 270:29).

In another embodiment, the antigen in the vaccine is a self-antigen. Such a vaccine is useful in the modulation of tolerance in an organism. Immunization with a self antigen and an agent that blocks Gal1 activity or interactions between a Gal1 polypeptide or a fragment thereof and its natural binding partner(s) or a fragment(s) thereof can break tolerance (i.e., interfere with tolerance of a self antigen). Such a vaccine may also include adjuvants such as alum or cytokines (e.g., GM-CSF, IL-12, B7-1, or B7-2).

In another embodiment, upregulation or enhancement of an immune response function, as described herein, is useful in the induction of tumor immunity (e.g., restoration of immune surveillance in Hodgkin lymphoma). Tumor cells (e.g., sarcoma, melanoma, lymphoma, leukemia, neuroblastoma, or carcinoma) can be transfected with a nucleic acid molecule that inhibits Gal1 activity or interactions between a Gal1 polypeptide or a fragment thereof and its natural binding partner(s) or a fragment(s) thereof. These molecules can be, e.g., nucleic acid molecules which are antisense to Gal1, or can encode non-activating anti-Gal1 antibodies or combinations of anti-Gal1 antibodies and antibodies against other immune related targets. These molecules can also be the variable region of an anti-Gal1 antibody and/or an anti-Gal1 antibody. If desired, the tumor cells can also be transfected with other polypeptides which enhance an immune response. The transfected tumor cells are returned to the patient, which results in inhibition (e.g., local inhibition) of Gal1 activity or interactions between a Gal1 polypeptide or a fragment thereof and its natural binding partner(s) or a fragment(s) thereof. Alternatively, gene therapy techniques can be used to target a tumor cell for transfection in vivo.

Stimulation of an immune response to tumor cells can also be achieved by inhibiting Gal1 activity or interactions between a Gal1 polypeptide or a fragment thereof and its natural binding partner(s) or a fragment(s) thereof, by treating a patient with an agent that inhibits Gal1 activity or interactions between a Gal1 polypeptide or a fragment thereof and its natural binding partner(s) or a fragment(s) thereof. Examples of such agents include, e.g., antisense nucleic acid molecules, small RNAs, antibodies that recognize and block Gal1, a combination of antibodies that recognize and block Gal1 and antibodies that recognize and block other immune related targets, compounds that block the interactions between a Gal1 polypeptide or a fragment thereof and its natural binding partner(s) or a fragment(s) thereof on an immune cell, and compounds identified in the subject screening assays).

In another embodiment, the immune response can be stimulated by the methods described herein, such that preexisting tolerance is overcome. For example, immune responses against antigens to which a subject cannot mount a significant immune response, e.g., to an autologous antigen, such as a tumor specific antigens can be induced by administering an agent that blocks interactions between a Gal1 polypeptide or a fragment thereof and its natural binding partner(s) or a fragment(s) thereof. In one embodiment, a blocking antibody that inhibits interactions between a Gal1 polypeptide or a fragment thereof and its natural binding partner(s) or a fragment(s) thereof can be used to enhance an immune response (e.g., to a tumor cell). In one embodiment, an autologous antigen, such as a tumor-specific antigen can be coadministered. In another embodiment, an immune response can be stimulated against an antigen (e.g., an autologous antigen) to treat an immune disorder, e.g., Hodgkin lymphoma. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

In an additional embodiment, in performing any of the methods described herein, it is within the scope of the invention to upregulate an immune response by administering one or more additional agents. For example, the use of other agents known to stimulate the immune response, such as cytokines, adjuvants, or stimulatory forms of costimulatory molecules or their ligands can be used in conjunction with an agent that inhibits Gal1 activity or a Gal1 polypeptide or a fragment thereof and its natural binding partner(s) or a fragment(s) thereof.

V. Administration of Agents

The immune modulating agents of the invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of a Gal1 blocking antibody may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents or the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays. In addition, an antibody of the invention can also be administered in combination therapy with, e.g., chemotherapeutic agents, hormones, antiangiogens, radiolabelled, compounds, or with surgery, cryotherapy, and/or radiotherapy. An antibody of the invention can also be administered in conjunction with other forms of conventional therapy, either consecutively with, pre- or post-conventional therapy. For example, the antibody can be administered with a therapeutically effective dose of chemotherapeutic agent. In another embodiment, the antibody can be administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regiment and dosages of these aforementioned chemotherapeutic drugs that are therapeutically effective will depend on the particular immune disorder, e.g., Hodgkin lymphoma, being treated, the extent of the disease and other factors familiar to the physician of skill in the art and can be determined by the physician.

This invention is further illustrated by the following examples which should not be construed as limiting. The contents of all references, patents and published patent applications cited throughout this application, as well as the Figures, are incorporated herein by reference.

EXAMPLES

Example 1

Materials and Methods used in Examples 1-5

A. Cell Lines

Figure 5:
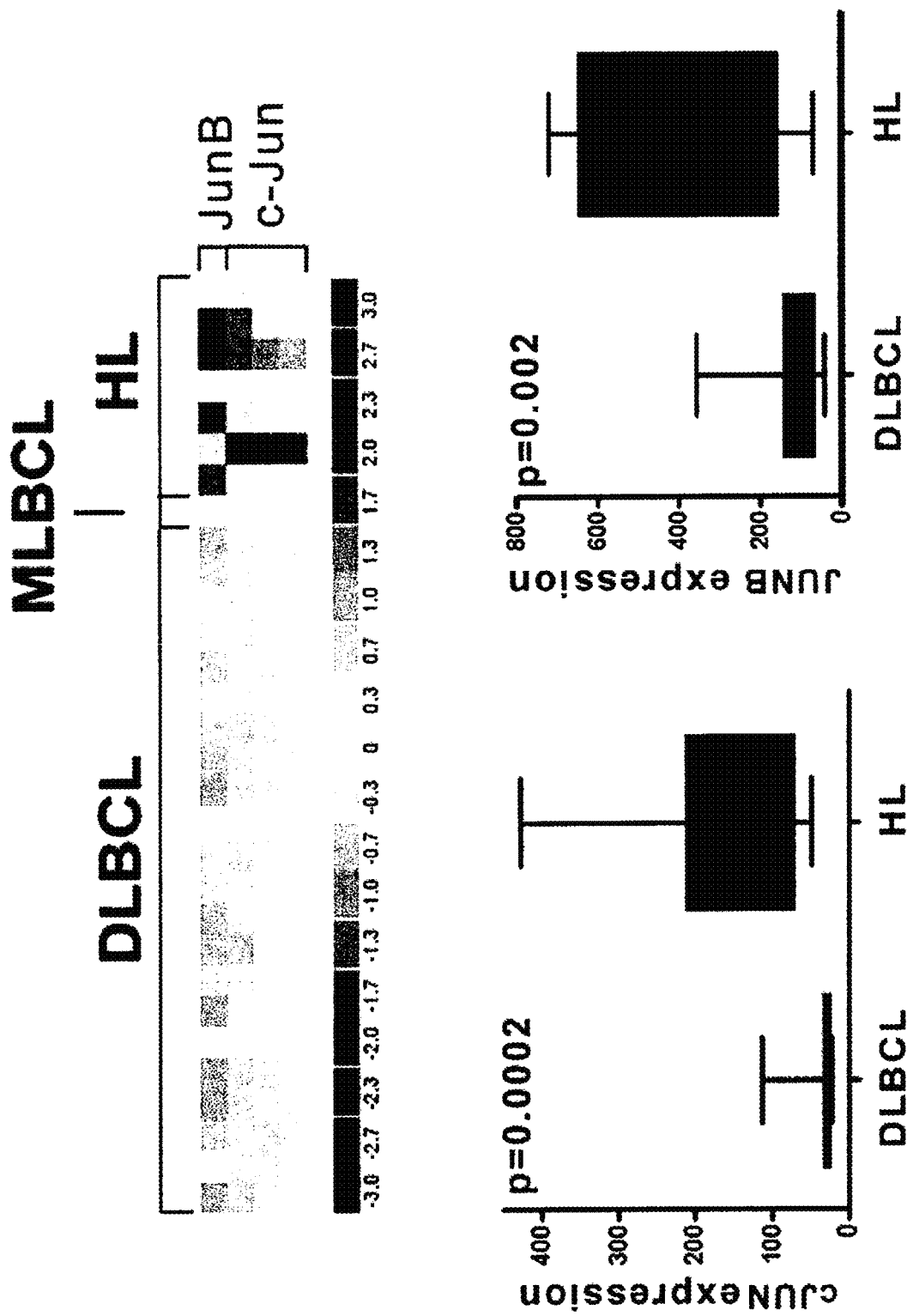
FIG. 5 shows cJUN and JUN-B expression in LBCL and cHL cell lines. The relative abundance of cJUN and JUN-B transcripts in DLBCL, MLBCL and cHL cell lines is shown. The color scale at the bottom indicates the relative expression and standard deviations from the mean. The plots represent the median expression of Gal1 (horizontal line) in LBCL versus cHL cell lines±25-75 percentile (bars) and ±range (whiskers). Statistical differences in the relative cJUN and JUN-B expression in DLBCL and cHL cell lines were evaluated using a Mann-Whitney U test.

Twenty-one DLBCL cell lines (Ly19, Ly18, Ly10, Ly8, Ly7, Ly4, Ly3, Ly1, Pleiffer, DHL10, DHL8, DHL7, DHL6, DHL5, DHL4, DB, HT WSU, Karpas 422, Toledo and Farage), 1 MLBCL cell line (Karpas 1106) and 7 cHL cell lines (KMH2, HDLM2, SupHD1, L1236, L540, L428, HD-MY-Z) were maintained as previously described (Mathas et al. (2002) *Embo J* 21, 4104-4113; Smith et al. (2005) *Blood* 105, 308-316). The cHL cell lines were previously demonstrated to have constitutive AP-1 activity and increased expression of c-JUN and JUNB (Mathas et al. (2002) *Embo J* 21, 4104-4113 and FIG. 5).

B. Identification of Genes Overexpressed in cHL Cell Lines by Gene Expression Profiling Total RNAs from a panel of 21 diffuse large B-cell lymphoma (DLBCL) and 7 cHL cell lines were hybridized to U133A and B Affymetrix oligonucleotide microarrays, and the chips were scanned and data analyzed as previously described (Monti et al. (2005) *Blood* 105, 1851-1861). The top 9,586 genes that met threshold and variation index criteria were analyzed with GenePattern program available on the World Wide Web at broad.mit.edu/cancer/software/genepattern/CEF) to identify differentially expressed genes in cHL and DLBCL. Genes correlated with the class template (HL vs. DLBCL) were identified by ranking them according to their signal-to-noise ratio (SNR). For each gene, a specific p-value based on permutation testing was calculated and corrected for false discovery rate by the Benjamini and Hochberg procedure (Benjamini et al. (2001) *Behav Brain Res* 125, 279-284; Reiner et al. (2003) *Bioinformatics* 19, 368-375).

C. Analysis of Gal1 Expression in Cell Lines by Immunoblot

DLBCL and cHL cell lines were maintained as previously described (Mathas et al. (2002) *Embo J* 21, 4104-4113; Polo et al. (2007) *Proc Natl Acad Sci USA* 104, 3207-3212). Cells were lysed, size-fractionated on NuPAGE Novex 4-12% Bis-Tris Gels (Invitrogen, Carlsbad, Calif.), and transferred to PVDF membranes (Millipore Corp., Bedford, Mass.). Membranes were immunostained with purified Gal1 rabbit IgG (Rubinstein et al. (2004) *Cancer Cell* 5, 241-251) and HRP-conjugated donkey anti-rabbit antibody (GE Healthcare, Piscataway, N.J.) and developed using a chemiluminescent method (ECL, GE Healthcare).

D. Immunohistochemistry

Immunohistochemistry was performed as previously described (Juszczynski et al. (2006) *Mol Cell Biol* 26, 5348-5359) using 5 μm thick formalin-fixed, paraffin-embedded tissue sections of newly diagnosed primary cHLs and DLBCLs and purified Gal1 rabbit IgG.

E. Analysis of Regulatory Elements in the Gal1 Locus and Generation of Gal1 Enhancer Constructs Computational analysis of the Gal1 locus (chr22:36,400, 510-36,406,802, alignment with Human NCBI Genome assembly v36, March 2006) was performed with the publicly available version of Genomatix suite available on the World Wide Web at genomatix.de) (Scherf et al. (2000) *J Mol Biol* 297, 599-606) and rVISTA available on the World Wide Web at rvista.dcode.org/) (Loots and Ovcharenko (2004) *Nucleic Acids Res* 32, W217-221) and a putative downstream regulatory element (enhancer) containing a conserved AP1 binding site was identified (+1567 to +1675). To generate a series of Gal1 promoter-enhancer reporter constructs, the Gal1 promoter region (−403+67) was amplified using PCR and this sequence was ligated into the pGL3 promoterless reporter vector (Promega, Madison, Wis.), generating pGL3-Gal1-403+67-Luc. Thereafter, fragments spanning nucleotides +459+1746, +459+777, and +1346+1746 from the Gal1 transcription start site (TSS) were PCR-amplified and cloned into pGL3-Gal1-403+67-Luc 3' of the luciferase gene. Deletions in AP1 site (TGACTCA to TGxxxCA) were generated using the pGL3-Gal1-403+67-Luc-e1346+1746 construct and the GeneTailor Site-Directed Mutagenesis System (Invitrogen) as recommended by the manufacturer. An additional set of constructs was generated with the candidate enhancer elements cloned upstream of the Gal1 promoter.

F. Generation of Dominant Negative cJun Constructs

Dominant-negative cJun constructs were generated as previously described (Ludes-Meyers et al. (2001) *Oncogene* 20, 2771-2780) with minor modifications. A cJun fragment which lacked the transactivation domain (amino acids 123 to 223) was PCR-amplified from intronless cJUN genomic DNA and ligated in the pFLAG-CMV2 vector (pFLAG-CMV2-cJUNDN) (Sigma Aldrich, St Louis, Mo.) using forward primer, CAAGAATTCCCAGAACACGCTGC-CCAGCGTC (SEQ ID NO: 4), and reverse primer, GAATCTAGAGTCGCAACTTGTCAAGT-TCTCAAGTCTGTC (SEQ ID NO: 5).

G. Analysis of Gal1 Promoter—Enhancer Constructs with Luciferase Assays

The HD-MY-Z cHL and SU-DHL7 DLBCL cell lines were grown to 60-80% confluency on 24 well-plates and cotransfected with 300 ng/well of the appropriate promoter-enhancer pGL3 construct (wild-type or mutant Gal1) and 100 ng/well of the control reporter plasmid, pRL-TK (Promega) using FuGENE 6 transfection reagent (Roche Applied Science) according to the manufacturer's protocol. For cotransfection experiments with cJUN-DN-FLAG, HD-MY-Z cells were transfected with 150 ng of pGL3-Gal1-403+67-Luc-e1346+1746, 250 ng of pFLAG-CMV2-cJUN-DN and 100 ng of pRL-TK. After 24 hours of incubation, cells were lysed and luciferase activities were determined by a chemiluminescence assay using the Dual Luciferase Assay kit (Promega) and Luminoskan Ascent luminometer (Thermo Lab Systems, Franklin, Mass.) as described (Juszczynski et al. (2006) *Mol Cell Biol* 26, 5348-5359).

H. Electrophoretic Mobility Shift Analyses of the AP1-Binding Site in the Gal1 Enhancer Nuclear extracts from three cHL cell lines (HD-MY-Z, L428 and SupHD-1) and 3 DLBCL cell lines (SU-DHL7, SU-DHL4 and Toledo) were obtained as previously described (Juszczynski et al. (2006) *Mol Cell Biol* 26, 5348-5359). Double-stranded wild-type (WT) and mutant probes corresponding to AP1-binding region in Gal1 enhancer (wild-type, WT [5'-TTTTCTGGGTGACTCACTTCCCCCG-3'] (SEQ ID NO: 6) and mutant, MUT [5'-TTTTCTGGGTcagtACT-TCCCCCG-3' (SEQ ID NO: 7) [mutant bases in lower case]) were end-labelled with [γ-$^{32}$P]ATP, purified and used in binding reactions as described (Juszczynski et al. (2006) *Mol Cell Biol* 26, 5348-5359). DNA binding was carried out using 5 μg of nuclear extracts and approximately 10,000 cpm of radiolabelled probe in 20 μL of binding buffer (Juszczynski et al. (2006) *Mol Cell Biol* 26, 5348-5359). After 30 minutes of incubation, reactions were loaded on a 5% polyacrylamide gel and electrophoresed. Gels were vacuum dried and exposed to x-ray films overnight at −80° C. For competitor studies, 100× molar excess of unlabelled wild-type or mutant probe was included in the binding reactions. For supershift studies, 1 μL of c-JUN antibody or β-actin (Santa Cruz Biotechnology, Santa Cruz, Calif. and Sigma-Aldrich, respectively) was added to the reaction 15 min prior to the probe.

I. Q-PCR Analysis of Gal1 Transcript Abundance Following AP1 Inhibition

The HD-MY-Z cHL cell line was grown to 60-80% confluency on 100 mm plates and transiently transfected with 15 μg of pFLAG-CMV2 (empty vector) or pFLAGCMV2-cJUNDN plasmids using FuGENE 6 transfection reagent (Roche Applied Science) according to the manufacturer's protocol. After 72 hours of culture, RNA was extracted using Trizol reagent (Invitrogen) and cDNA was synthesized from total RNA (3 μg) using SuperScript II reverse transcriptase (Invitrogen) and random hexamer primers. Gal1 and GAPDH (housekeeping control) transcript abundance was evaluated by QPCR using Power SYBR green PCR Master Mix (Applied Biosystems, Foster City, Calif.) and the following primers: GAPDH, Forward: GATTCCACCCATGGCAAATTC (SEQ ID NO: 8); GAPDH, Reverse: TGATTTTGG AGG-GATCTCGCTC (SEQ ID NO: 9); Gal1, Forward: TCGC-CAGCAACCTGAATCTC (SEQ ID NO: 10), Gal1, Reverse: GCACGAAGCTCTTAGCGTCA (SEQ ID NO: 11). PCR was performed using an ABI 7700 thermal cycler (Applied Biosystems) and threshold Cycle ($C_T$) values were generated using the Sequence Detection Software, version 1.2 (Applied Biosystems). Gal1 transcript abundance was calculated relative to the housekeeping control GAPDH using the $2^{-(\Delta CTGal1 - \Delta CTGAPDH)}$ method according to the manufacturer's instructions. Standard deviations were calculated from triplicate ΔCT values.

J. RNA-Interference Mediated Gal1 Knock-Down

Gal1 specific siRNA was designed using siRNA Selection Program (Yuan et al. (2004) *Nucleic Acids Res* 32, W130-134) (available on the World Wide Web at jura.wi.mit.edu/bioc/siRNAext/), synthesized as single-stranded DNA oligonucleotides by Integrated DNA Technologies (IDT, Inc., Coralville, Iowa) and annealed. Gal1-specific oligonucleotide (Gal1 RNAi, GATCCGCTGCCAGATGGATAC-GAATTCAAGAGATTCGTATCCATCTG-GCAGCTTTTTTG (SEQ ID NO: 12) or scrambled oligonucleotide (SCR, GATCCCCTC-CATATCTCGCGCGTCTTCAA-GAGAGACGCGCGAGATATGGAGGTTTTTTG (SEQ ID NO: 13) were ligated into the linearized pSIREN-RetroQ retroviral vector (BD Clontech, Mountain View, Calif.). Generation of recombinant retrovirus and infection of HD-MY-Z cells was performed as previously described (Juszczynski et al. (2006) *Mol Cell Biol* 26, 5348-5359). After infection, cells were subjected to puromycin selection (0.5 µg/mL) and subcloning by limiting dilution. Thereafter, whole-cell extracts of obtained subclones were prepared and screened for Gal1 expression by immunoblotting as described above. Gal1 knockdown did not alter the proliferation rate or viability of transduced HD-MY-Z cells.

K. Co-Cultures and Analyses of T-Cell Responses in cHL Microenvironment

1. Co-culture. Peripheral blood mononuclear cells (PBMCs) were obtained from normal blood donors by Ficoll-Hypaque (GE Healthcare) gradient centrifugation. Thereafter, T cells were purified using Pan T Cell Isolation Kit II (Miltenyi Biotec, Auburn, Calif.) and activated with 1 µg/mL PHA (Sigma-Aldrich) for 64 hours. $1 \times 10^6$ of activated T cells were then co-cultured with monolayers ($3 \times 10^6$ cells) of HD-MY-Z cells expressing either scrambled shRNA or Gal1 specific shRNA for 6 hours at 37° C.

2. Analyses of viable T cells. Following co-culture, all cells were harvested and sequentially stained with CD3-PE and CD4-PE-Cy5 (Beckman Coulter, Fullerton, Calif.) followed by Annexin V-FITC and analyzed with a Beckman Cytomics FC500 flow cytometer. The numbers of viable (annexin V-) and (propidium iodide-) $CD3^+$ and $CD4^+$ T cells in Gal1 shRNA or scrambled shRNA HD-MY-Z/T-cell co-cultures were then compared.

3. Analyses of T-bet and GATA-3 expression in co-cultured $CD4^+$ T cells. After PHA-activated T-cells were co-cultured with HD-MY-Z cells expressing either scrambled shRNA or Gal1 specific shRNA for 24-48 hours, cells were collected and non-viable cells were depleted by Ficoll-Hypaque gradient centrifugation. Remaining viable cells were washed, incubated with CD4 MACS microbeads and purified using a MACS LS column according to the manufacturer's protocol (Miltenyi Biotec). Thereafter, RNA was obtained from the isolated $CD4^+$ cells and cDNA was synthesized from total RNA (3 µg) as described above. GATA-3, T-bet and GAPDH (housekeeping control) transcript abundance was evaluated by QPCR using Power SYBR green PCR Master Mix (Applied Biosystems, Foster City, Calif.), GAPDH primers listed above and the following GATA3 and T-bet primers: GATA3, Forward: TAACATCGACGGTCAAGGCA (SEQ ID NO: 14); GATA3, Reverse: ACACCTGGCTCCCGTGGT (SEQ ID NO: 15); T-bet, Forward: TGGACGTGGTCTTGGTG-GACC (SEQ ID NO: 16); T-bet, Reverse: TGGACGTACAG-GCGGTTTCC (SEQ ID NO: 17). PCR and transcript abundance analysis was performed as described above. GATA-3 and T-bet expression in purified $CD4^+$ cells from SCR shRNA and Gal1 shRNA HD-MY-Z/T-cell cocultures were then compared.

L. Cytokine Production in T-Cell Subpopulations Treated with rGal1

Recombinant Gal1 was obtained and purified essentially as described (Toscano et al. (2006) *J Immunol* 176, 6323-6332). T cells were purified as described above and simultaneously activated with anti-CD3-(0.1 µg/mL) and anti-CD28-(0.5 µg/mL) coated latex beads (Invitrogen) and treated with rGal1 (20 µM) in RPMI 1640 medium containing 10% fetal bovine serum and 1 mM β-ME alone or rGal1 and the Gal1 inhibitor, thiodigalactoside (TDG, 100 mM) (Rabinovich et al. (1999) *J Exp Med* 190, 385-397) or left untreated for 16 hours. Supernatants were then analyzed for IL-4, IL-5, IL-10, and IL-13 using cytometric bead array (CBA) Flex Set beads according to manufacturer's protocol (BD Biosciences, San Jose, Calif.). In brief, multiplexed antibody-conjugated beads were incubated with culture supernatants or serial dilutions of cytokine standards for 1 hour. Thereafter, the PE detection reagent was added and samples were incubated for an additional 2 hours, washed and analyzed using FACS Aria Flow Cytometer (BD Biosciences). Results were captured with FACS Diva software and analyzed with the FCAP1.1 program (BD Biosciences).

M. Analyses of Regulatory T Cells ($T_{regs}$)

T cells were purified, activated with anti-CD3- and anti-CD28-coated latex beads and treated with rGal1, rGal1 and TDG or left untreated for 24 hours. Thereafter, cells were stained with CD4-FITC and CD25-APC, washed, fixed, permeabilized and stained with FOXP3-PE antibody or rat IgG2b isotype control as previously described (Zorn et al. (2006) *Blood* 108, 1571-1579) (Human Regulatory T-cell staining kit, eBioscience, San Diego, Calif.). $CD4^+$ $CD25^{high}$ FOXP3 $T_{reg}$ cells were identified and quantified using Beckman Cytomics FC500 flow cytometer as previously described (Zorn et al. (2006) *Blood* 108, 1571-1579).

N. Statistical Analysis

All statistical analyses were done using Statistica 6.0 software (Statistica, Tulsa, Okla.). Students t test was used for comparisons between 2 groups; Anova was used for multiple comparisons.

Example 2

Overexpression of Gal1 in cHL RS Cells

To identify novel cHL-specific T-cell inhibitory molecules, the gene expression profiles of a series of cHL and diffuse large B-cell lymphoma (DLBCL) and mediastinal LBCL (MLBCL) cell lines were compared. Gal1 transcripts were 4- to 29-fold more abundant in cHL cell lines than in the LBCL lines (p=0.002, FDR=0.014, FIGS. 1A and 1B). Gal1 protein expression was also uniformly high in cHL cell lines and low or undetectable in DLBCL and MLBCL lines by western blotting (FIG. 1C). Immunohistochemical staining of primary tumor sections revealed abundant Gal1 expression in cHL RS cells, whereas LBCLs were uniformly negative (FIG. 1D). In a series of primary lymphoid tumors, 10/10 cHLs were Gal1$^+$ whereas 10/10 primary DLBCLs and 5/5 primary mediastinal LBCLs (MLBCLs) lacked Gal1 expression. Taken together, these data indicate that Gal1 is selectively upregulated in the RS cells of cHLs.

Example 3

RS Cell Gal1 Expression is Regulated by an AP1-Dependent Enhancer

Figure 2:
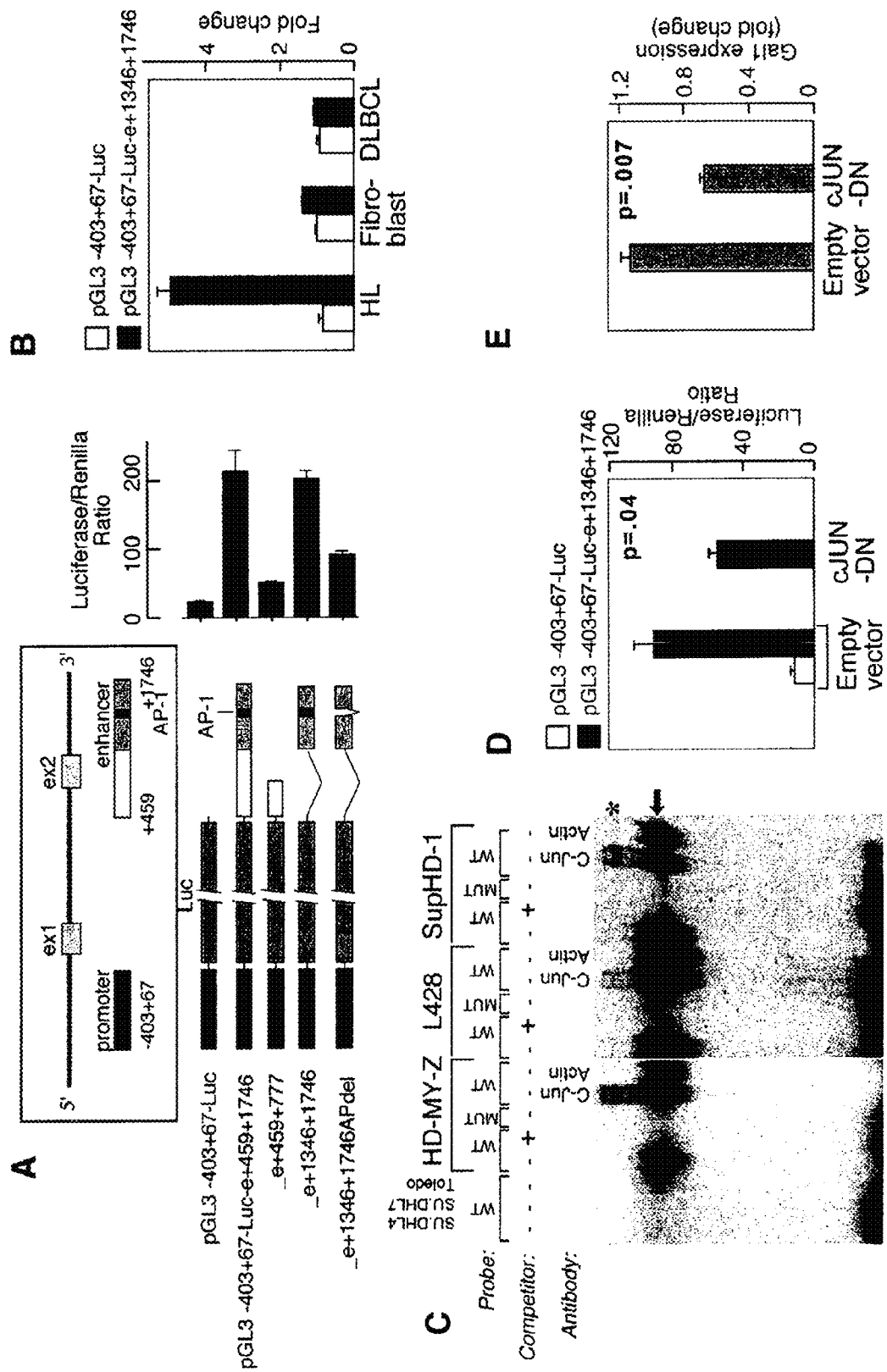
FIGS. 2A-2E shows that Gal1 transcription is regulated by an AP1-dependent enhancer.

To elucidate the mechanisms responsible for Gal1 overexpression in cHL RS cells, the Gal1 locus on chromosome 22 was analyzed. A candidate GC-rich regulatory element with a conserved putative AP1 binding site approximately 1.5 kb downstream of the Gal1 transcription start site (TSS) was identified. Since the AP1 components, cJUN and JUN-B are overexpressed in cHL and are critical for the pathogenesis of the disease (Mathas et al. (2002) *EMBO J.* 21: 4104-4113), it was asked whether AP1 mediates Gal1 expression in cHL. Luciferase vectors driven by the previously described Gal1 promoter (−403+67) were generated (Salvatore et al. (1998) *FEBS Lett* 421:152-8) and the putative Gal1 enhancer element (or mutated controls) and assessed associated luciferase activity in a cHL cell line (HD-MY-Z) known to have constitutive activation of AP1 (FIG. 2A) (Mathas et al. (2002) *EMBO J.* 21: 4104-4113). Constructs including the GC-rich regulatory element (bp+459+1746 or +1346+1746) upregulated luciferase expression 8-10 fold, whereas constructs lacking the candidate sequence (+459+777) or containing a deletion in the AP1-binding site (+1346+1746$_{del}$) exhibited significantly lower luciferase activity (FIG. 2A). Similar results were obtained with a set of constructs in which the regulatory element was cloned upstream of the Gal1 promoter, demonstrating that the identified sequence (bp+1346+1746) is a bona fide Gal1 enhancer.

Given the AP1 dependence of the Gal1 enhancer and the constitutive AP1 activity in cHL (Mathas et al. (2002) *EMBO J.* 21: 4104-4113), it was next asked whether the Gal1 enhancer was selectively active in this disease. For these experiments, cHL, DLBCL and fibroblast cell lines were transfected with either the Gal1 promoter-only vector (pGL3-Gal1$_{403+67}$-Luc) or the promoter-enhancer construct (pGL3-Gal1$_{403+67}$-Luc-e$_{1346+1746}$) and compared the respective luciferase activities (FIG. 2B). The Gal1 promoter-enhancer construct specifically upregulated luciferase expression in cHL cells but not DLBCL cells or fibroblasts (FIG. 2B).

After demonstrating the specificity and activity of the Gal1 AP1 enhancer element in a cHL cell line (FIGS. 2A and 2B), the requirement for AP1 transcription factors in electrophoretic mobility shift assays was directly evaluated (FIG. 2C). Nuclear extracts from 3 cHL and 3 DLBCL cell lines were incubated with radiolabelled wild-type or mutant probes corresponding to an AP1 element in the Gal1 enhancer. Gal1 wild type, but not mutant probe, directly bound to nuclear proteins extracted from cHL, but not DLBCL, cell lines (FIG. 2C). The complexes formed with Gal1 WT probe were displaced by unlabeled WT competitor, further confirming the binding specificity (FIG. 2C). In supershift assays, the Gal1/AP1 complex was retarded by cJun antibody (FIG. 2C). Furthermore, the simultaneous overexpression of a dominant negative cJUN construct (cJUN-DN) reduced Gal1-driven luciferase activity in cHL cells (FIG. 2D). In addition, when AP1 was at least partially inhibited via the overexpression of cJUN-DN, there was a significant decrease in Gal1 transcript abundance in cHL cells (FIG. 2E). Taken together, these studies indicate that cHL RS cells selectively overexpress Gal1, at least in part, via an AP1-driven enhancer.

Example 4

Figure 3:
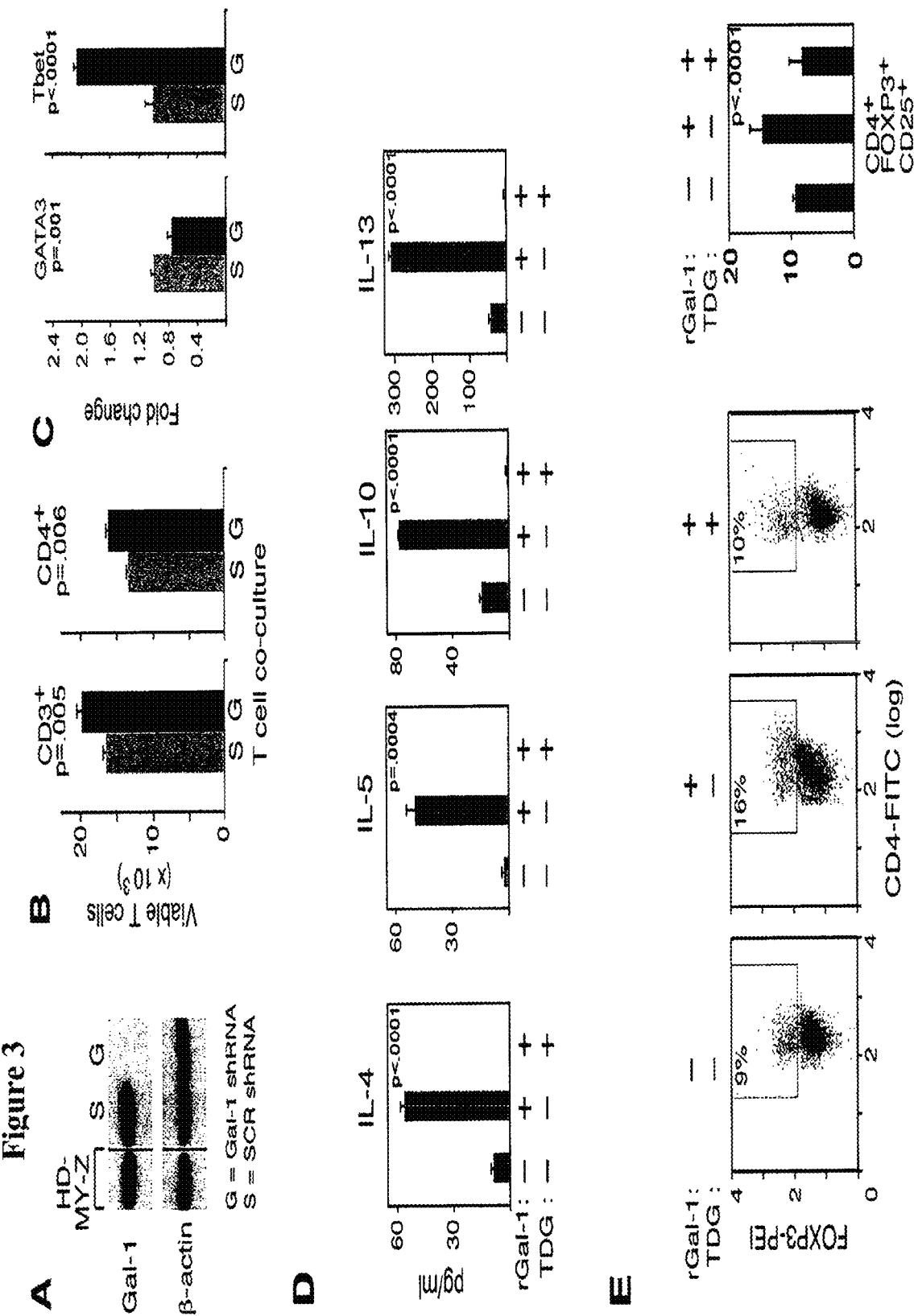
FIGS. 3A-3C shows that Gal1 confers immune privilege to cHL Reed-Sternberg cells by favoring the expansion of Th2 cells and T$_{reg}$ cells.
FIG. 3D shows the production of Th2 cytokines by Gal1-treated T cells. Activated T cells were either untreated or treated with rGal1 in the presence or absence of TDG. Th2 cytokine (IL-4, IL-5, IL-10 and IL-13) production was then assessed using cytometric bead arrays.
FIG. 3E shows the abundance of T$_{reg}$ cells in Gal1-treated T cells. Activated T cells were cultured in the presence of rGal1, rGal1+TDG or left untreated. The percentage of CD4$^+$ CD25$^+$ FOXP3$^+$ T-cells was then assessed by triple color-flow cytometry. Representative histograms (left) and summary statistics (right) are shown.

Endogenous cHL Gal1 Expression Contributes to the Immunosuppressive and Th2-Skewed Microenvironment in Classical Hodgkin Lymphoma After delineating the mechanism for cHL-specific overexpression of Gal1, the functional consequences of cHL RS cell Gal1 expression on the associated inflammatory/immune infiltrate was assessed. Stable HD-MY-Z transfectants expressing Gal1 specific shRNA (Gal1 shRNA) or a scrambled control shRNA (SCR, FIG. 3A) were generated. Activated T-cell blasts were then added to Gal1 shRNA or SCR HD-MY-Z cells grown as adherent monolayers and the cHL line and T cells were co-cultured. Thereafter, total T-cell and Th-cell viabilities were assessed using 3-color Annexin-V, -CD3 and -CD4 flow cytometry. There were significantly fewer viable total (CD3$^+$) and Th (CD4$^+$) T cells in control (SCR) HD-MY-Z co-cultures than in co-cultures of HD-MY-Z cells with Gal1 knockdown (FIG. 3B). These studies directly demonstrate that endogenous cHL RS cell Gal1 decreases the viability of infiltrating activated T cells.

Given the skewed nature of inflammatory infiltrate in cHL, it was asked whether endogenous cHL RS cell Gal1 may contribute to this Th1/Th2 imbalance. To address this question, CD4$^+$ Th cells were isolated from the cHL/T-cell co-cultures and the relative expression of the Th1- and Th2-specific transcription factors, T-bet and GATA-3, was analyzed by RQ-PCR. CD4$^+$ Th cells co-cultured with control (SCR) HD-MY-Z cells exhibited significantly lower expression of T-bet and higher expression of GATA-3 than CD4$^+$ T cells from Gal1 shRNA HD-MY-Z co-cultures (FIG. 3C). Taken together, these results indicate that endogenous cHL RS cell Gal1 selectively decreases the viability of associated Th1 cells resulting in a skewed Th2-type infiltrate.

Example 5

Figure 4:
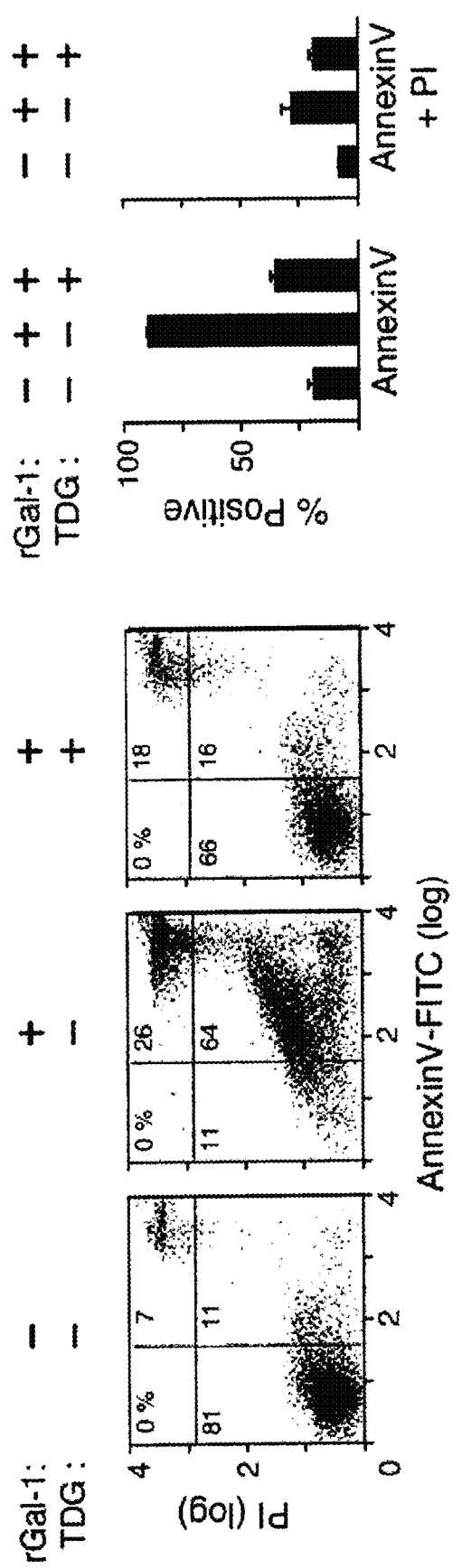
FIG. 4 shows that recombinant Gal1 induces apoptosis in normal activated T-cells. Activated T-cells were either untreated or treated with rGal1 in the presence or absence of TDG. Thereafter, apoptosis was assessed by FITC-annexin V and PI double staining. The histograms (left panels) are representative of 3 separate experiments that were averaged to obtain the percent positive cells in the bar graphs (right panels).

Gal1 Promotes Immune Privilege by Favoring the Secretion of Th2 Cytokines and the Expansion of CD4$^+$ CD25$^{high}$ FOXP3$^+$ T$_{regs}$ Given the profound immunosuppressive activity of Gal1 in Th1/Th17-mediated autoimmune settings (Rabinovich et al. (1999) *J Exp Med* 190:385-397; Toscano et al. (2006) *J Immunol* 176:6323-6332; Santucci et al. (2003) *Gastroenterol* 124: 1381-1394), it was asked whether this glycan-binding protein was directly implicated in the skewed Th2 cytokine profile associated with primary cHL. For this purpose, activated T cells were treated with recombinant Gal1 (rGal1) in the presence or absence of the Gal1 inhibitor, thiodigalactoside (TDG) (Rabinovich et al. (1999) *J Exp Med* 190:385-397). As expected, rGal1 induced apoptosis of total activated T cells (FIG. 4). Concurrent treatment with TDG completely blocked rGal1-induced apoptosis, confirming the specificity of the Gal1 effect (FIG. 4). Th2 cytokines in supernatants from activated T cells that were untreated or treated with rGal1 in the presence or absence of TDG were subsequently quantified. Supernatants from rGal1-treated T cells contained significantly higher amounts of the Hodgkin-associated Th2 cytokines, IL-4, IL-5, IL-10 and IL-13, and TDG specifically blocked this effect (FIG. 3D). These data further support the hypothesis that RS cell Gal1 expression promotes Th2-type cytokine production in primary cHLs.

In addition to Th2 cells, the inflammatory infiltrate in primary cHL includes abundant T regulatory cells (CD4$^+$ CD25$^{high}$ FOXP3$^+$) that directly blunt the host anti-tumor immune response (Marshall et al. (2004) *Blood* 103:1755-1762; Gandhi et al. (2006) *Blood* 108:2280-2289, Ishida et al. (2006) *Cancer Res* 66:5716-5722; Gabrilovich, D. (2007) *Curr Cancer Drug Targets* 7: 1). Therefore, the role of Gal1 in the selective expansion of T$_{reg}$ cells was assessed using the above-mentioned assay. Activated T cells were treated with rGal1 in the presence or absence of TDG and analyzed thereafter for T$_{regs}$ (CD4$^+$ CD25$^{high}$ FOXP3$^+$) using triple-color immunofluorescence as described (Zorn et al. 2006) *Blood* 108:1571-1579). The CD4$^+$ CD25 high FOXP3 population was significantly increased in rGal1 treated cells and TDG completely blocked this effect (FIG. 3E). Taken together, these results demonstrate that Gal1 fosters the skewed and immunosuppressive microenvironment in cHL by enhancing the production of Th2 cytokines (IL-4, IL-5, IL-10 and IL-13) and increasing the relative abundance of $T_{reg}$ cells.

Examples 1-5 describe the overexpression of Gal1 by cHL RS cells and identify the mechanism as a phylogenetically conserved AP1 responsive enhancer. In functional in vitro assays, it has been shown that cHL RS cell Gal1 decreased the viability of activated T cells and skewed the balance towards a Th2 immune response. Consistent with this observation, Gal1 markedly increased the secretion of Th2 cytokines including IL-4, IL-5, IL-10 and IL-13. In addition, Gal1 fostered the expansion and/or retention of $CD4^+$ $CD25^{high}$ $FOXP3^+$ $T_{reg}$ cells. Taken together, these data directly implicate RS cell Gal1 in the development and maintenance of the unique $Th2/T_{reg}$-skewed immunosuppressive microenvironment in primary cHL.

Although cHL RS cells exhibit near uniform Gal1 expression, DLBCLs and MLBCL are largely Gal1 negative, prompting speculation that Gal1 may distinguish cHL from certain "grey zone" lymphomas that share characteristics of DLBCL and cHL (Abramson and Shipp (2005) Blood 106, 1164-1174). A common feature of these "grey zone" lymphomas is an increased host inflammatory response, highlighting the interaction between the tumor cells and their host microenvironment (Abramson and Shipp (2005) Blood 106, 1164-1174). Gal1 overexpression is a defining feature of cHL that is not shared with its closely related counterpart, primary MLBCL (Savage et al. (2003) Blood 102, 3871-3879), providing insights into the relative efficacy of host immune responses in these tumors.

The differential expression of Gal1 in these lymphomas is likely due to the cHL-specific overexpression of the AP1 transcription factor components, cJUN and JUNB, and the constitutive activation of the AP1 pathway (Mathas et al. (2002) Embo J 21, 4104-4113). Gal1 expression is regulated, at least in part, by a cHL-specific, AP1-driven enhancer. AP1 also functions in synergy with NF-κB to control the proliferation and limit the apoptosis of cHL RS cells (Mathas et al. (2002) Embo J 21, 4104-4113). Therefore, in addition to its pro-survival functions in cHL RS cells, AP1 also regulates the interplay between RS cells and the tumor microenvironment through a Gal1-mediated pathway.

RS Gal1 is likely to be a critical factor shaping the immuno- and histopathologic features of primary cHL. Endogenous RS cell Gal1 specifically induced the apoptosis of activated T lymphocytes, suggesting that a similar mechanism operates in primary cHLs and that these tumors represent sites of immune privilege. Gandhi et al. also recently described increased Gal1 expression in cHL (Gandhi et al. (2007) Blood, First Edition Paper online Apr. 16, 2007).

The short-term in vitro assays likely underestimate the long-term in vivo effects of Gal1 in cHL because the lectin is also deposited in the extracellular matrix and stroma where it kills susceptible T cells (He and Baum (2004) J Biol Chem 279, 4705-4712). In in vitro assays, Gal1 expressing RS cells selectively decreased the viability of infiltrating Th1 cells resulting in a Th2-predominant infiltrate. Consistent with the observed reduction in Th1 cells and enrichment in Th2 cells, Gal1 significantly increased the levels of the Th2 cytokines, IL-4, IL-5, IL-10 and IL-13. The Gal1-associated cytokine profile suggests that this glycan-binding protein may have additional functions beyond modulating T-cell responses in primary cHLs. Since IL-13 is a critical RS cell growth factor (Skinnider et al. (2002) Leuk Lymphoma 43, 1203-1210), Gal1 may indirectly stimulate tumor growth by fostering the production of this Th2 cytokine. Via its effect on another Th2 cytokine, IL-5, Gal1 may also promote the characteristic eosinophilic infiltrate in primary cHL (von Wasielewski et al. (2000) Blood 95, 1207-1213).

The observations regarding Gal1 function in cHL are consistent with recent reports regarding the role of the lectin in murine models of Th1-driven chronic inflammatory and autoimmune disorders including collagen-induced arthritis, inflammatory bowel disease, graft vs. host disease and autoimmune uveitis (Rabinovich et al. (1999) J Exp Med 190:385-397; Toscano et al. (2006) J Immunol 176:6323-6332; Santucci et al. (2003) Gastroenterol 124: 1381-1394; Baum et al. (2003) Clin Immunol 109:295-307). In these studies, the administration of Gal1 dramatically suppressed Th1-dependent responses and skewed towards Th2 cytokine profiles (Rabinovich et al. (1999) J Exp Med 190:385-397; Toscano et al. (2006) J Immunol 176:6323-6332; Santucci et al. (2003) Gastroenterol 124: 1381-1394; Baum et al. (2003) Clin Immunol 109:295-307; van der Leig et al. (2006) Mol Immunol 10, 1-8). A careful examination of the mechanisms involved in Gal1-mediated Th2-skewing recently revealed that Th1 cells express the repertoire of cell surface glycans required for Gal1 binding and subsequent cell death, whereas Th2 cells are protected from Gal1 via differential sialylation of their cell surface glycoproteins (Toscano et al. (2007) Nature Immunol, Published online: 24 Jun. 2007).

In addition to the Th2 shift, the results provide the first evidence showing that Gal1 treatment increases the relative abundance of $CD4^+$ $CD25^{high}$ FOXP3 $T_{reg}$ cells that may blunt the host anti-cHL immune response. It is possible that the specific glycosylation pattern of Gal1 receptors on $T_{regs}$ renders them resistant to Gal1-induced apoptosis. In fact, $T_{regs}$ have been reported to exhibit increased α2,6 sialylation (compared to effector T cells) (Jenner et al. (2006) Exp Hematol 34, 1211-1217); this selective sialylation might interfere with Gal1 binding and cell death (Amano et al. (2003) J Biol Chem 278, 7469-7475). This hypothesis is further supported by recent studies demonstrating that $T_{regs}$ overexpress Gal1 and remain resistant to Gal1-mediated apoptosis (Garin et al. (2007) Blood 109, 2058-2065).

Taken together, the data described herein provide new insights into the biology of RS cells and identifies a key AP1-dependent mechanism regulating cHL-specific immune privilege. Since Gal1 blockade dramatically increased tumor rejection in recently described murine models (Rubinstein et al. (2004) Cancer Cell 5, 241-251), it is possible that Gal1 inhibition may augment host anti-tumor responses in primary cHL. Furthermore, this lectin is likely to have additional roles in the biology of cHL. Recent studies indicate that Gal1 also promotes tumor cell motility and enhances tumor angiogenesis (Liu and Rabinovish, (2005) Nature Reviews Cancer 5, 29-41; Rabinovich (2005) Br J Cancer 92, 1188-1192; Thijssen et al. (2006) Proc Natl Acad Sci USA 103, 15975-15980; Camby et al. (2002) J Neuropathol Exp Neurol 61, 585-596), processes critical for tumors like cHL that spread by contiguous involvement of adjacent nodes and organs. Gal1, thus, represents a new rational therapeutic target in cHL.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for modulating an immune response comprising contacting an immune cell from a subject having Hodgkin lymphoma in vitro with an agent that modulates the interaction between galectin-1 (Gal1) or a fragment thereof and its natural binding partner(s), wherein the agent is a blocking antibody, or an antigen-binding fragment thereof, that recognizes Gal1, and wherein the agent does not comprise a Hodgkin lymphoma-specific antigen, an antigen-binding molecule thereof, or an immune cell obtained from the subject, to thereby modulate the immune response.

2. The method of claim 1, wherein the immune response is upregulated.

3. The method of claim 1, further comprising contacting the immune cell with an additional agent that upregulates an immune response.

4. A method for treating a subject having Hodgkin lymphoma comprising administering an agent that inhibits the interaction between galectin-1 (Gal1) and its natural binding partner(s) on cells of the subject, wherein the agent is a blocking antibody, or an antigen-binding fragment thereof, that recognizes Gal1, and wherein the agent does not comprise a Hodgkin lymphoma-specific antigen, an antigen-binding molecule thereof, or an immune cell obtained from the subject, such that the Hodgkin lymphoma is treated.

5. The method of claim 4, further comprising administering a second agent that upregulates an immune response in the subject.

6. The method of claim 4 further comprising a chemotherapy treatment.

* * * * *

SEQUENCE LISTING

```
<160> NUMBER OF SEQ ID NOS: 17

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctgccagat ggatacgaa                                                      19

<210> SEQ ID NO 2
<211> LENGTH: 408
<212> TYPE: DNA
<213> ORGANISM: Homo sapiens
<220> FEATURE:
<221> NAME/KEY: CDS
<222> LOCATION: (1)..(408)

<400> SEQUENCE: 2 atg gct tgt ggt ctg gtc gcc agc aac ctg aat ctc aaa cct gga gag        48
Met Ala Cys Gly Leu Val Ala Ser Asn Leu Asn Leu Lys Pro Gly Glu
1               5                   10                  15 tgc ctt cga gtg cga ggc gag gtg gct cct gac gct aag agc ttc gtg        96
Cys Leu Arg Val Arg Gly Glu Val Ala Pro Asp Ala Lys Ser Phe Val
            20                  25                  30 ctg aac ctg ggc aaa gac agc aac aac ctg tgc ctg cac ttc aac cct       144
Leu Asn Leu Gly Lys Asp Ser Asn Asn Leu Cys Leu His Phe Asn Pro
        35                  40                  45 cgc ttc aac gcc cac ggc gac gcc aac acc atc gtg tgc aac agc aag       192
Arg Phe Asn Ala His Gly Asp Ala Asn Thr Ile Val Cys Asn Ser Lys
    50                  55                  60 gac ggc ggg gcc tgg ggg acc gag cag cgg gag gct gtc ttt ccc ttc       240
Asp Gly Gly Ala Trp Gly Thr Glu Gln Arg Glu Ala Val Phe Pro Phe
65                  70                  75                  80 cag cct gga agt gtt gca gag gtg tgc atc acc ttc gac cag gcc aac       288
Gln Pro Gly Ser Val Ala Glu Val Cys Ile Thr Phe Asp Gln Ala Asn
                85                  90                  95 ctg acc gtc aag ctg cca gat gga tac gaa ttc aag ttc ccc aac cgc       336
Leu Thr Val Lys Leu Pro Asp Gly Tyr Glu Phe Lys Phe Pro Asn Arg
            100                 105                 110 ctc aac ctg gag gcc atc aac tac atg gca gct gac ggt gac ttc aag       384
Leu Asn Leu Glu Ala Ile Asn Tyr Met Ala Ala Asp Gly Asp Phe Lys
        115                 120                 125 atc aaa tgt gtg gcc ttt gac tga                                        408
Ile Lys Cys Val Ala Phe Asp
    130                 135

<210> SEQ ID NO 3
<211> LENGTH: 135
<212> TYPE: PRT
<213> ORGANISM: Homo sapiens

<400> SEQUENCE: 3
```

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
                20                  25                  30

Leu Asn Leu Gly Lys Asp Ser Asn Asn Leu Cys Leu His Phe Asn Pro
            35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65              70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
                100                 105                 110

Leu Asn Leu Glu Ala Ile Asn Tyr Met Ala Ala Asp Gly Asp Phe Lys
        115                 120                 125

Ile Lys Cys Val Ala Phe Asp
    130             135

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caagaattcc cagaacacgc tgcccagcgt c                                    31

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaatctagag tcgcaacttg tcaagttctc aagtctgtc                            39

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ttttctgggt gactcacttc ccccg                                           25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ttttctgggt tcagtacttc ccccg                                           25

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gattccaccc atggcaaatt c                                            21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgattttgga gggatctcgc tc                                           22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcgccagcaa cctgaatctc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcacgaagct cttagcgtca                                              20

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gatccgctgc cagatggata cgaattcaag agattcgtat ccatctggca gcttttttg   59

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gatcccctcc atatctcgcg cgtcttcaag agagacgcgc gagatatgga ggttttttg   59

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taacatcgac ggtcaaggca                                                 20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acacctggct cccgtggt                                                   18

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggacgtggt cttggtggac c                                               21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tggacgtaca ggcggtttcc                                                 20
```